US008239000B1

(12) United States Patent
Morris et al.

(10) Patent No.: US 8,239,000 B1
(45) Date of Patent: Aug. 7, 2012

(54) DIMENSIONAL APPROACH TO IDENTIFYING EMOTIONAL RESPONSES USING FUNCTIONAL BRAIN IMAGING

(76) Inventors: Jon D. Morris, Gainesville, FL (US); Yijun Liu, Gainesville, FL (US)

( * ) Notice: Subject to any disclaimer, the term of this patent is extended or adjusted under 35 U.S.C. 154(b) by 1119 days.

(21) Appl. No.: 11/726,663

(22) Filed: Mar. 21, 2007

Related U.S. Application Data

(60) Provisional application No. 60/784,246, filed on Mar. 21, 2006.

(51) Int. Cl.
*A61B 5/05* (2006.01)
(52) U.S. Cl. .................................................. 600/410
(58) Field of Classification Search .................. 600/410
See application file for complete search history.

(56) References Cited

U.S. PATENT DOCUMENTS

| | | | |
|---|---|---|---|
| 6,099,319 A * | 8/2000 | Zaltman et al. | 434/236 |
| 6,292,688 B1 | 9/2001 | Patton | |
| 2005/0154290 A1 | 7/2005 | Langleben | |
| 2006/0036153 A1 * | 2/2006 | Laken | 600/410 |

OTHER PUBLICATIONS

Bernston et al., "Respiratory sinus arrhythmia: Autonomic origins, physiological mechanisms, and psychophysiological implications" *Psychophysiology*, 1993, pp. 183-196, vol. 30.
Cacioppo et al., "Relationship Between Facial Expressiveness and Sympathetic Activation in Emotion: A Critical Review, With Emphasis on Modeling Underlying Mechanisms and Individual Differences" *J. of Personality and Social Psychology*, 1992, pp. 110-128, vol. 62, No. 1.
Decety et al "Neural correlates of feeling sympathy" *Neuropsychologia*, 2003, pp. 127-138, vol. 41.
Graham et al., "Heart-Rate Change as a Component of the Orienting Response" *Psychological Bulletin*, 1966, pp. 305-320, vol. 65, No. 5.
Iidaka et al., "Neural Interaction of the Amygdala with the Prefrontal and Temporal Cortices in the Processing of Facial Expressions as Revealed by fMRI" *J. of Cog. Neurosci.*, Nov. 15, 2001, pp. 1035-1047, vol. 13, No. 8.
Lane et al., "Neuroanatomical correlates of pleasant and unpleasant emotion" *Neuropsychologia*, 1997, pp. 1437-1444, vol. 35, No. 11.
Matthews et al., "Functional subdivisions within anterior cingulated cortex and their relationship to autonomic nervous system function" *NueroImage*, 2004, pp. 1151-1156, vol. 22, No. 3.

(Continued)

*Primary Examiner* — Tse Chen
*Assistant Examiner* — Hien Nguyen
(74) *Attorney, Agent, or Firm* — Saliwanchik, Lloyd & Eisenschenk

(57) ABSTRACT

The present invention concerns methods for evaluating the emotional response to stimuli, such as marketing communications. The present invention includes a method for correlating an emotional response to brain imaging data, a method identifying an emotional response to a stimulus, and a system for identifying an emotional response to a stimulus. The present invention can incorporate a psychological non-verbal measure, such as AdSAM®, and a neural-physiological measure, functional brain imaging, such as functional magnetic resonance imaging (fMRI), positron emission tomography (PET), or other functional brain imaging modality. For example, in marketing communication research, the emotional response data can be determined for such things as product concepts, advertising (concept and/or finished ads), product attributes, product benefits, brands, logos, tag lines, packaging, music, etc. The method of the invention can also be used to assess emotional response to different purchase options (e.g., retail vs. online), lifestyle issues, product usage situations, and other scenarios. In personnel management studies, the method of the invention can be used to measure employee satisfaction or employee morale.

23 Claims, 8 Drawing Sheets

OTHER PUBLICATIONS

McDonald et al., "Projections of the Medial and Lateral Prefrontal Cortices to the Amygdala: A *Phaseolus vulgaris* Leucoagglutinin Study in the Rat" *Neuroscience*, 1996, pp. 55-75, vol. 71, No. 1.

Mitchell et al., "The neural response to emotional prosody, as revealed by functional magnetic resonance imaging" *Neuropsychologia*, 2003, pp. 1410-1421, vol. 41.

Morris, "Observations: SAM: The Self-Assessment Manikin" *J. of Advertising Res.*, 1995, pp. 63-68, vol. 35, No. 6.

Morris et al., "A neuromodulatory role for the human amygdale in processing emotional facial expressions" *Brain*, 1998, pp. 47-57, vol. 121.

Morris et al., "Elaboration likelihood model: A missing intrinsic emotional implication" *J. of Targeting, Measurement & Analysis for Marketing*, Dec. 2005, pp. 79-98, vol. 14. No. 1.

Morris et al., "The Power of Affect: Predicting Intention" *J. of Advertising Res.*, 2002, pp. 7-17, vol. 42, No. 3.

Nomura et al., "Frontal lobe networks for effective processing of ambiguously expressed emotions in humans" *Neuroscience Letters*, 2003, pp. 113-116, vol. 348.

Obrist et al., "The Cardiac-Somatic Relationship: Some Reformulations" *Psychophysiology*, 1970, pp. 569-587, vol. 6, No. 5.

Ojemann et al., "Neurons in Human Temporal Cortex Active with Verbal Associative Learning" *Brain and Language*, 1998, pp. 317-327, vol. 64.

Paradiso et al., "Emotional Activation of Limbic Circuitry in Elderly Normal Subjects in a PET Study" *Amer. J. of Psychiatry*, 1997, pp. 384-389, vol. 154, No. 3.

Phan et al., "Review Functional Neuroanatomy of Emotion: A Meta-Analysis of Emotion Activation Studies in PET and fMRI" *NeuroImage*, 2002, pp. 331-348, vol. 16, No. 2.

Shaver at al., "Emotion Knowledge: Further Exploration of a Prototype Approach" *J. of Personality and Social Psychology*, 1987, pp. 1061-1086, vol. 52, No. 6.

Sprengelmeyer et al., "Neural structures associated with recognition of facial expressions of basic emotions" *Proceedings of the Royal Society of London, Series B: Biological Sciences*, Oct. 22, 1998, pp. 1927-1931, vol. 265, No. 1409.

Sundar et al., "Arousal, Memory, and Impression-Formation Effects of Animation Speed in Web Advertising" *J. of Advertising*, 2004, pp. 7-17, vol. 33.

Adolphs, R. "Recognizing Emotion from Facial Expressions: Psychological and Neurological Mechanisms" *Behavioral and Cognitive Neuroscience Reviews*, Mar. 1, 2002, pp. 21-62. vol. 1, No. 1.

Bowers, D. et al., "Differential Impact of Right and Left Hemisphere Lesions on Facial Emotion and Object Imagery" *Brain*, Dec. 1991, pp. 2593-2609, vol. 114, No. 6.

Bradley, M.M. et al., "Measuring emotion: Behavior feeling, and physiology" *In Cognitive Neuroscience of Emotion*, R.D. Lane, and L. Nadel, eds., 2000, pp. 242-276, New York, Oxford University Press.

Bradley, M.M. et al., "Affective Picture Processing" *In the Structure of Emotion: Psycho Physiological, Cognitive, and Clinical Aspects*, N. Birbaumer and A. Ohman, eds., 1994, pp. 48-65, Toronto: Hugute-Huber.

Devinsky, O. et al., "Contributions of anterior cingulated cortex to behaviour" *Brain*, 1995, pp. 279-306, vol. 118.

Frijda, N.H., "Physiology of Emotion" *The Emotions*, 1986, pp. 124-175, New York: Cambridge University Press.

Frijda, N.H. et al. "Neurophysiological conditions" *The Emotions*, 1986, pp. 379-400, New York: Cambridge University Press.

George, M.S. et al., "Understanding emotional prosody activates right hemisphere regions" *Arch Neurol.*, 1996, pp. 665-670, vol. 53, No. 7.

Hasselmo, M.E. et al., "The role of expression and identity in the face-selective responses of neurons in the temporal visual cortex of the monkey" *Behav. Brain Res.*, 1989, pp. 203-218, vol. 32.

Izard, "The emotions in life and science" *Human Emotions*, 1977, pp. 1-18, New York: Plenum Press.

Lacey, J.I. et al., "The visceral level: Situational determinants and behavioral correlates of autonomic response patterns" *Expression of the emotions in man*, P.H. Kapp ed., New York: International Universities Press, 1963, pp. 161-196.

Lane et al., "Neuroanatomical correlates of happiness, sadness, and disgust" *Ameri. J. of Psychiatry*, 1997, pp. 926-933, vol. 154.

Lang, P.J. "The Cognitive Psychophysiology of Emotions: Fear and Anxiety" *Anxiety and the Anxiety Disorders*, 1985, pp. 131-169, Hillsdale, NJ: Lawrence Erlbaum.

Lang, P.J. "Behavioral treatment and bio-behavioral assessment: Computer applications" *Technology in mental health care delivery systems*, J.B. Sidowski, J.H. Johnson, T.A. Williams Eds., 1980, pp. 119-137, Norwood, NJ: Ablex.

Ledoux, J.E. et al., "Indelibility of Subcortical Emotional Memories" *J. of Cognitive Neuroscience*, 1989, pp. 238-243, vol. 1, No. 3.

Mandler, G. *Mind and Body: Psychology of Emotion and Stress*, 1984, pp. 1-14, New York: Norton.

Morris, J.D. et al., "Assessing emotional responses to advertisements with (SAM) the self-assessment manikin" *In Proceedings of the Allied Southern business Association*, Annual Meeting: Allied Southern Business Association, 1993, pp. 2-27.

Osgood, C.E. et al., *The Measurement of Meaning*, 1957, pp. 1-75, Urbana, IL, University of Illinois Press.

Plutchik, R. "A general psychoevolutionary theory of emotion" In R. Plutchik & H. Kellerman Eds., *Emotion: Theory, Research, and Experience*, New York: Academic, 1980, pp. 3-33, vol. 1.

Plutchik, R. "Emotions: A general psychoevolutionary theory" In Kr.R. Scherer & P. Ekman Eds., *Approaches to Emotion*, 1984, pp. 197-219, Hillsdale, NJ: Lawrence, Erlbaum Associates.

Russell, J.A. et al., "Evidence for a three-factor theory of emotions" *Journal of Research in Personality*, 1977, pp. 273-294, vol. 11.

Stemmler, "The Analysis of Activation" *Differential psychophysiology: Persons in situations*, 1992, pp. 187-241 and pp. 339-363, New York: Springer-Verlag.

Tomkins, "Affect as amplification: Some modifications in theory" In R. Plutchik & H. Kellerman Eds., *Emotion: Theory, Research and Experience*, 1980, pp. 141-164, vol. 1, New York: Academic Press.

\* cited by examiner

DIMENSIONAL APPROACH TO IDENTIFYING EMOTIONAL RESPONSES USING FUNCTIONAL BRAIN IMAGING

CROSS-REFERENCE TO RELATED APPLICATION

The present application is claims the benefit of U.S. Provisional Application Ser. No. 60/784,246, filed Mar. 21, 2006, which is hereby incorporated by reference herein in its entirety, including any figures, tables, and drawings.

BACKGROUND OF THE INVENTION

Emotional response research has been an area of active research for decades. Some of the research has used self-reporting techniques. Izard (Izard, C. E. "The emotions in life and science" In Human emotions, C. E. Izard, ed., New York, Plenum Press, 1977, pp. 1-18) and Plutchik (Plutchik, R. "Emotions: A general psychoevolutionary theory" In Approaches to emotion, K. R. Scherer, and P. Ekman, eds., Hillsdale, N.J., Lawrence Erlbaum Associates, 1984, pp. 197-219) both used a discrete self-reporting approach that focused on specific emotions such as happiness and anger. Others have used a more robust three-dimensional self-report approach (Osgood, C. E. et al. "The measurement of meaning" Urbana, Ill., University of Illinois Press, 1958; Russell, J. A. and Mehrabian, A. *Journal of Research in Personality*, 1977, 11:273-294; Sundar, S. S., and Kalyanaraman, S. *Journal of Advertising*, 2004, 33:7-17). Other research has measured emotional response using physiological measures. Agreement between self-reporting and physiological measurements would provide convergent validity for both methods. However, to date, a link between the two measures of emotion has not been fully explored.

The search for physiological links to emotion reflects an approach that seeks fundamental or discrete emotions (Mandler, G. "Mind and body" New York, Norton, 1984). Subcortical emotional responses are amply recorded through classical conditioning of fear reactions to audio or visual stimuli (LeDoux, J. E. et al. *Journal of Cognitive Neuroscience*, 1989, 1:238-243). The responses either interrupt the cognitive focus of current attention or influence the context for ongoing cognitive processes (Simon, H. A. Comments. In Affect and cognition: The seventeenth annual Carnegie symposium on cognition, M. S. Clarke, and S. T. Fiske, eds., Hillsdale, N.J., Erlbaum, 1982, pp. 333-342). Pleasant and unpleasant emotional responses were found to increase neural activity in the medial prefrontal cortex, thalamus, and hypothalamus, while unpleasant emotions were found to increase the neural activity in the occipitotemporal cortex, parahippocampal gyms, and amygdale (Lane, R. D. et al. *Neuropsychologia*, 1997, 35:1437-1444). Additionally, facial expressions of disgust or anger were found to increase the neural activity in the left inferior frontal gyrus (Sprengelmeyer, R. et al. *Proceedings of the Royal Society of London, Series B: Biological Sciences*, 1998, 265:1927-1931). A meta-analysis of emotion activation studies in PET and fMRI (Phan, K. L. et al. *NeuroImage*, 2002, 16:331-348) concluded that no single brain region is activated by all emotions, and no single brain region is activated by one particular emotion.

The discrete approach assumes categorical judgment of emotional stimuli. This requires connections between both hemisphere (Bowers, D. et al. *Brain*, 1991, 114:2593-2609) and between the anterior cingulated cortex and the bilateral prefrontal cortex (Devinsky, O. et al. *Brain*, 1995, 118:279-306). Therefore, certain brain regions might be activated because of the demand to categorize or label discrete emotions rather than the natural emotional responses to given stimuli. Furthermore, most neuroimaging studies treat emotions as two discrete categories—pleasant and unpleasant—while ignoring the nuances along the pleasure dimension and the additional explanatory power of the arousal and dominance dimensions. For example, intensity of fear has been associated with brain activities in the left inferior frontal gyrus (Morris, J. S. et al. *Brain*, 1998, 121:47-57) while anger and disgust have been associated with difference degrees of intensity or arousal (Iidaka, T. et al. *Journal of Cognitive Neuroscience*, 2001, 13:1035-1047).

The alternative three-dimensional approach to emotion attempts to simplify the representation of responses by identifying a set of common dimensions that can be used to distinguish specific emotions from one another. This approach, which includes both verbal and non-verbal measures (Lang, P. J. Behavioral treatment and bio-behavioral assessment: Computer applications. In Technology in mental health care delivery systems, J. B. Sidowski, J. H. Johnson, and T. A. Williams, eds., Norwood, N.J., Ablex, 1980, pp. 119-137; Osgood, C. E. et al. The measurement of meaning, Urbana, Ill., University of Illinois Press, 1958; Russell, J. A., and Mehrabian, A. *Journal of Research in Personality*, 1977, 11:273-294), has been largely ignored in research.

One example of the approach is a pleasure-displeasure, arousal-calm, and dominance-submissiveness (PAD) model (Russell, J. A., and Mehrabian, A. *Journal of Research in Personality*, 1977, 11:273-294). The three bi-polar dimensions are independent of each other, and the variance of emotional responses can be well identified with their positions along the three dimensions. The dimensional approach helps differentiate emotions posited by the discrete approach (Shaver, P. et al. *Journal of Personality and Social Psychology*, 1987, 52:1061-1086) by providing a numeric level of each dimension to describe the specific emotions. Each discrete emotion can be identified by specific combinations of the dimensions. The meaning of these specific adjectives may differ by individual, culture or some other influence; however, the method for identifying the response is universal. Understanding the reactions by dimensions, as first proposed by Osgood, Suci, and Tannenbaum (Osgood, C. E. et al. The measurement of meaning, Urbana, Ill., University of Illinois Press, 1958), makes the analysis methodologically meaningful.

Neuroimaging techniques, such as positron emission tomography (PET) and functional magnetic resonance imaging (fMRI), are reported in a growing body of emotion literature. Regional cerebral blood flow (rCBF) signals of PET and blood oxygenation level-dependent (BOLD) signals of fMRI are used to identify possible links between brain regions and emotions. It is worthwhile to point out that the search for these links reflects a Darwinian approach to emotions, which seeks evolutionarily fundamental or discrete emotions (Mandler, G. (1984) *Mind and body*. New York: Norton; Plutchik, R. (1980) "A general psychoevolutionary theory of emotion" In R. Plutchik & H. Kellerman (Eds.), *Emotion: Theory, research, and experience*, Vol. 1, pp. 3-33, New York: Academic), and the alternative three-dimensional approach with verbal or non-verbal measures (Lang, P. J. (1980) "Behavioral treatment and bio-behavioral assessment: Computer applications" In J. B. Sidowski, J. H. Johnson & T. A. Williams (Eds.), *Technology in mental health care delivery systems* (pp. 119-137), Norwood, N.J.: Ablex; Morris, J. D. et al. (1993) "Assessing emotional responses to advertisements with (SAM) the self-assessment manikin" In *Proceedings of the Allied Southern Business Association* 1993 *Annual Meet-*

*ing*: Allied Southern Business Association; Morris, J. D. et al. (2002) *Journal of Advertising Research*, 42(3):7-17; Osgood, C. E. et al. (1958), *The measurement of meaning*. Urbana, Ill.: University of Illinois Press; Russell, J. A. and Mehrabian, A. (1977) *Journal of Research in Personality*, 11:273-294) is largely ignored.

With the discrete approach to emotions, researchers have used visual, audio, and video stimuli and reported mixed findings about the links in question. For example, when visual stimuli such as facial emotional expressions were used, both pleasant and unpleasant emotions were found to increase brain activities in the medial prefrontal cortex, thalamus, hypothalamus, whereas unpleasant emotions were found to increase the activities in the occipitotemporal cortex, parahippocampal gyms, and amygdale (Lane, R. D. et al. (1997) *Neuropsychologia*, 35(11):1437-1444). Additionally, facial expressions of disgust or anger were found to increase the activities in the left inferior frontal gyms (Sprengelmeyer, R. et al. (1998) *Proceedings of the Royal Society of London, Series B: Biological Sciences*, 265:1927-1931). When audio stimuli such as speech were used, emotional responses to the auditory information of a speech, such as intonation, loudness, and tempo, were found to increase brain activities in the inferior frontal gyms whereas emotional responses to the semantic information of the speech were found to increase brain activities in the middle frontal gyms (George, M. S. et al. (1996) *Archives of Neurology*, 53:665-670). Additionally, the middle temporal gyms was found to integrate the processing of both the auditory and the semantic information of the speech as well as information from past memories and interpret the meaning of the speech (Mitchell, R. L. C. et al. (2003) *Neuropsychologia*, 41:1410-1421; Ojemann, G. A. and Schoenfield-McNeill, J. (1998) *Brain and Language*, 64:317-327). When both audio and visual stimuli such as video clips were used, fear, disgust, and sadness were found to increase brain activities in orbitofrontal cortex, medial prefrontal cortex, and thalamus, whereas happiness was found to increase the activities in the entorhinal cortex, the medial prefrontal cortex, and thalamus (Lane, R. D. et al. (1997) *American Journal of Psychiatry*, 154:926-933; Paradiso, S. et al. (1997) *American Journal of Psychiatry*, 154:384-389). Moreover, the semantic information of video clips was found to increase brain activities in the inferior frontal gyrus and the very use of dynamic stimuli such as video clips is more likely to induce brain activities in the inferior frontal gyrus than are still face images (Adolphs, R. (2002) *Behavioral and Cognitive Neuroscience Reviews*, 1:21-62; Decety, J. and Chaminade, T. (2003) *Neuropsychologia*, 41:127-138).

As summarized in a meta-analysis of emotion activation studies in PET and fMRI (Phan, K. L. et al. (2002) *NeuroImage*, 16:331-348), no single brain region is activated by all emotions, nor is a single brain region activated by one specific emotion. Nevertheless, from a cortical emotional learning perspective, three brain regions, namely the amygdala, prefrontal cortex, and temporal cortex, are particularly important, especially for video clips. First, the prefrontal cortex has been found to have neural projections to the amygdale (McDonald, A. J. et al. (1996) *Neuroscience*, 71:55-75), and the temporal cortex has been found to send stimulus information to the prefrontal cortex (Hasselmo, M. E. et al. (1989) *Behavioral Brain Research*, 32:203-218). Second, the temporal cortex has been found to allow the brain to merge perceptual and semantic information, past memories and short-term manipulation of the stimuli (Mitchell, R. L. C. et al. (2003) *Neuropsychologia*, 41:1410-1421). Finally, both the semantic information and the dynamic nature of video clips have been found to increase brain activities in the prefrontal cortex (Adolphs, R. (2002) *Behavioral and Cognitive Neuroscience Reviews*, 1:21-62; Decety, J. and Chaminade, T. (2003) *Neuropsychologia*, 41:127-138).

As mentioned above, the discrete approach to emotions dominates the current neuroimaging studies. However, there are conceptual problems with this approach and researchers would propose different types of discrete emotions. For example, they could be a set of eight emotions—interest, surprise, joy, anguish, fear, shame, disgust, and rage (Tomkins, S. S. (1980) "Affect as amplification: Some modifications in theory" In R. Plutchik & H. Kellerman (Eds.), *Emotion: Theory, research and experience*. New York: Academic Press), or another set of eight emotions—fear, anger, joy, sadness, acceptance, disgust, anticipation, and surprise (Plutchik, R. (1984) "A general psychoevolutionary theory" In K. R. Scherer & P. Ekman (Eds.), *Approaches to emotion*, Hillsdale, N.J.: Lawrence, Erlbaum Associates), or even another set of ten emotions—interest, joy, surprise, distress, anger, disgust, contempt, shame, fear, and guilt (Izard, C. E. (1977) "The emotions in life and science" In C. E. Izard (Ed.), *Human emotions* (pp. 1-18), New York: Plenum Press). The disagreement on either the number or the kinds of emotions across the three lists seems to suggest a lack of well-accepted theoretical ground to support the notion of discrete emotions (Mandler, G. (1984). *Mind and body*. New York: Norton).

Alternatively, the present inventors have found that the dimensional approach to emotions exists in the brain. This approach will simplify the representation of emotional responses by identifying a set of common dimensions that can be used to distinguish specific emotions from one another. Two of three bi-polar independent dimensions have been identified in discrete locations in the brain. Levels of pleasure-displeasure, arousal-calm, (PA) (Russell, J. A. and Mehrabian, A. (1977) *Journal of Research in Personality*, 11:273-294) have been measured and located. As a matter of fact, the dimensional approach, such as the PA, helps differentiate separate emotions posited by the discrete approach by combining levels of pleasure and arousal (Shaver, P. et al. (1987) *Journal of Personality and Social Psychology*, 52(6): 1061-1086).

Brain activity identified using the dimensional approach provides a very promising new perspective for investigation, specifically measuring issues ignored and under-explored in previous neuroimaging studies. For example, categorical judgment of emotional stimuli requires connections between both hemispheres (Bowers, D. et al. (1991) *Brain*, 114:2593-2609) and between the anterior cingulated cortex and the bilateral prefrontal cortex (Devinsky, O. et al. (1995) *Brain*, 118:279-306); therefore, certain brain regions may be activated by natural reactions to given stimuli, as levels of pleasure, arousal and dominance rather than discrete emotions. Furthermore, most neuroimaging studies treat emotions as falling into two large categories of pleasant or unpleasant and ignore the nuance along the pleasure dimension and the additional explanatory power of the arousal and dominance dimensions. For instance, it has been found that brain activities in the left inferior frontal gyms would be enhanced when the intensity of fearful facial expression is increased (Morris, J. S. et al. (1998) *Brain*, 121:47-57) and anger and disgust have varying degree of intensity (Iidaka, T. et al. (2001) *Journal of Cognitive Neuroscience*, 13(8):1035-1047). The association between arousal, which well represents intensity, and brain regions can now be investigated in a systematic manner.

Another line of emotional response research focuses on somatovisceral reactions to emotional stimuli. These reactions are primarily autonomic nervous system (ANS) activities such as heart rate, sweating, and digestive processes (Zajonc, R. B. et al. (1993) "Brain temperature and subjective emotional experience" In M. Lewis & J. M. Haviland (Eds.), *Handbook of emotions*. New York: Guilford Press). Similar to the dominant approach in neuroimaging studies, researchers again attempted to identify ANS activities of discrete emotions. Unfortunately, this attempt is not very successful. For example, the ANS activity may vary as a function of the intensity of emotions rather than specific emotions per se. When the influence of specific emotions on ANS activities is weak or the influence in question is not strictly additive, changes in ANS activities are largely due to non-emotional factors such as individual differences (Cacioppo, J. T. et al. (1992) *Journal of Personality and Social Psychology*, 62:110-128; Stemmler, D. G. (1992) *Differential psychophysiology: Persons in situations*. New York: Springer-Verlag), anticipated or actual somatic activities (Obrist, P. A. et al. (1970) *Psychophysiology*, 6:569-587), respiration (Bernston, G. C. et al. (1993) *Psychophysiology*, 30:183-196), and attention (Graham, F. K. and Clifton, R. K. (1966) *Psychological Bulletin*, 65:305-320; Lacey, J. I. et al. (1963) "The visceral level: Situational determinants and behavioral correlates of autonomic response patterns" In P. H. Kapp (Ed.), *Expression of the emotions in man* (pp. 161-196), New York: International Universities Press). The ANS activities may also be a function of the perception of specific emotions because anticipated or realized action requirements of an emotional challenge would determine physiological responses to the stimulus (Frijda, N. H. (1986). *The emotions*. New York: Cambridge University Press; Lang, P. J. et al. (1990) *Psychological Review*, 97:377-395). Because there are strong correlations between brain activities and ANS activities (Matthews, S. C. et al. (2004) *NeuroImage*, 22(3):1151-1156), it is not surprising to note the insufficiency of the discrete approach to emotions in defining emotion-specific ANS activities, which again leads to the present inventors' advocacy of the dimensional approach to emotions.

Methods for detecting emotional response to stimuli based on brain activity using functional brain imaging and other techniques have been developed. See, for example, U.S. Pat. No. 6,099,319 (Zaltman and Kosslyn, filed Nov. 9, 1998, "Neuroimaging as a Marketing Tool"), U.S. Pat. No. 6,292,688 (Patton, filed Feb. 28, 1996, "Method and Apparatus for Analyzing Neurological Response to Emotion-Inducing Stimuli"), and U.S. Patent Publication US 2005/0154290 A1 (Langleben, filed Jun. 17, 2002, "Functional Brain Imaging for Detecting and Assessing Deception and Concealed Recognition, and Cognitive/Emotional Response to Information").

It would be advantageous to have available a method for assessing emotional response that incorporates two independent measures, both a psychological, non-verbal measure and a neural-physiological measure, in order to cross-validate and to correct for scale bias or measurement errors associated with single measure approaches.

BRIEF SUMMARY OF THE INVENTION

As described herein, the present inventors propose that the three-dimensional self-report approach to emotions is not only a sound methodology but, in fact, parallels key physiological functions in the brain. The findings provide a promising new perspective for investigating issues that have been unexplored or vaguely defined in previous neuroimaging studies.

Previously, blood oxygenation level-dependent (BOLD) signals from functional magnetic resonance imaging (fMRI) of emotional response to stimuli have been identified by looking for location-specific emotional reactions (ER), such as happy, sad, angry and afraid, in the brain. The present invention is based on a three-dimensional technique that is used in self-reporting of emotional response (AdSAM®). The dimensions are: pleasure (also known as valance), arousal, and dominance. These dimensions were first identified in the literature in the mid-fifties, and were labeled evaluation, activation and surgency. The present invention is based on a unique paradigm for studying ER in brain imaging and can provide a new understanding of brain function and new treatment options for brain diseases.

Unlike approaches that are based on fMRI alone, the present invention can incorporate a psychological non-verbal measure, such as AdSAM®, and a neuro-physiological measure, functional brain imaging such as fMRI. A significant advantage of using two independent measures is that it enables cross-validation to correct for scale bias or measurement errors associated with single measure approaches. Thus, the present invention uses an accepted technique to develop new research tools.

Applying the paradigm to an individual exposed to stimuli such as an advertisement or other media information, the data that is generated can be used to interpret the effect of the information on that individual. This permits the effective manipulation of the content of the media information to achieve maximal desired impact in target populations or on specific individuals.

Accordingly, one aspect of the invention pertains to a method for identifying an emotional response to a stimulus, comprising exposing a selected subject to a stimulus; monitoring the subject with a brain imaging device, such as an fMRI device or a positron emission tomography (PET) device, while exposing the subject to the stimulus; collecting data from the brain imaging device; providing the subject with a questionnaire (also referred to herein as a survey) to determine the subject's emotional response score (e.g., PAD score), wherein the questionnaire is completed by the subject; and correlating the data from the questionnaire with the data from the brain imaging device. The subject can be provided with the questionnaire, and can complete the questionnaire, while the subject is being exposed to the stimulus or after the subject is exposed to the stimulus. The subject can be provided with the questionnaire, and can complete the questionnaire, while the subject is being monitored with the brain imaging device or after the subject is monitored with the brain imaging device.

In the methods and system of the invention, the stimulus to which the subject is exposed can be of a form such as visual, auditory, tactile, olfactory, taste, or a combination or two or more of the foregoing. In one embodiment, the stimulus is a media communication such as a marketing communication. For example, the stimulus can be a product or service concept, advertising (concept and/or finished ads), product or service attributes, product or service benefits, brands, logos, tag lines, packaging, music (such as a theme song or jingle), etc. In one embodiment, the stimulus is a full-length video advertisement, or a portion thereof. In another embodiment, the stimulus is the scent of a perfume or cologne. In another embodiment, the stimulus is an attorney's and/or witness's potential communication before a judicial authority and/or jury in a courtroom, tribunal, etc. (such as an attorney's opening statement, attorney's closing statement, attorney's direct examination, attorney's cross-examination, witness testimony, etc.).

In another embodiment, the stimulus is a description of an environment, situation, behavior, or a combination of two or more of the foregoing. For example, the stimulus can be a description of a hypothetical environment, description of an actual environment, description of a hypothetical situation, description of an actual situation, description of hypothetical behavior, or a description of an actual behavior.

Optionally, in any of the embodiments, the methods of the invention can further comprise selecting the individual from a group of individuals based on one or more predefined parameters such as age, income level, gender, education, occupation, race, nationality, political affiliation, sexual orientation, height, weight, health, level of daily or weekly exercise, geographic domicile, etc.

BRIEF DESCRIPTION OF THE DRAWINGS

The patent or application file contains at least one drawing executed in color. Copies of this patent or patent application publication with color drawings will be provided by the Office upon request and payment of the necessary fee.

FIGS. 1A and 1C are traces showing % BOLD signal vs. time (scans). FIG. 1B shows locations of the activity and p value.

FIGS. 2A and 2C are traces showing % BOLD signal vs. time (scans). FIG. 2B shows the locations of the activity and p value.

FIG. 3A shows the locations of the activity and p value. FIG. 3B is a trace showing % BOLD signal vs. time (scans).

FIG. 4A shows the locations of the activity and p value. FIG. 4B is a trace showing % BOLD signal vs. time (scans).

FIG. 5A illustrates that the Anti-Fur commercial is significantly lower than the other four commercials on mean Pleasure scores, and FIG. 5B illustrates that that the Gatorade and Anti-Fur commercials combined are significantly higher than the Teacher and Coke commercials combined on mean Arousal scores.

DETAILED DESCRIPTION OF THE INVENTION

Figures 1A, 1B, 1C:
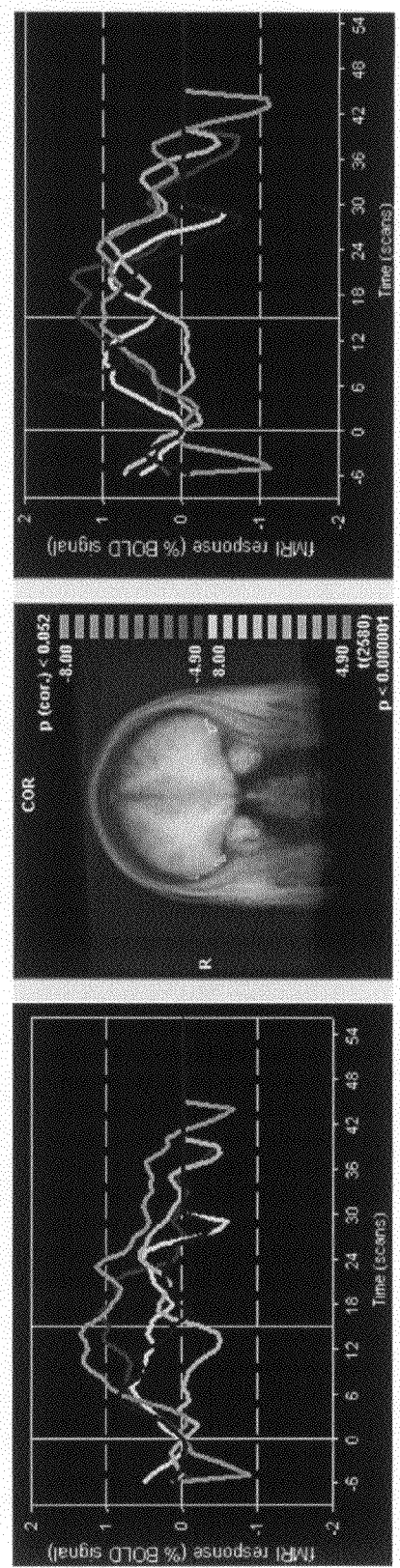
FIGS. 1A-1C are fMRI results showing bilateral activity in response to the stimulus.

Insights into emotional responses help in developing strategies, identifying drivers for perceptions, attitudes, and behaviors. The emotional response in conjunction with other key measures provides a more complete picture of what is occurring.

In one aspect, the invention concerns a method for correlating an emotional response to brain imaging data, comprising exposing a subject to a stimulus; monitoring the subject with a brain imaging device to obtain brain imaging data; determining the subject's emotional response score for the stimulus; and correlating the subject's emotional response score with the brain imaging data to determine a relationship there between.

In another aspect, the invention concerns a method for identifying an emotional response to a stimulus, comprising exposing a subject to a stimulus; monitoring the subject with a brain imaging device to obtain brain imaging data; and determining the subject's emotional response score for the stimulus based on the brain imaging data. Correlation of emotional response to brain imaging data will facilitate identification of emotional response to s stimulus based merely on the brain imaging data and the knowledge of which brain regions are associated with the various dimensions of emotional response and to what extent (e.g., for a given class or demographic of subject).

Preferably, the subject(s) are human. However, other mammals can be used in the subject invention, such as non-human primates.

Preferably, the imaging device is a functional magnetic resonance imaging (fMRI) device. Preferably, the emotional response score is a pleasure, arousal, and/or dominance (PAD) score. In one embodiment, the subject's emotional response score is determined by a non-verbal measurement system. In another embodiment, the subject's emotional response score is determined by a verbal measurement system (e.g., having the subject select a value on a continuum (e.g., 1-5 or 1-9) for one or more emotional dimensions (pleasure, arousal, and or dominance). In one embodiment, the subject's emotional response score is determined by having the subject complete a questionnaire while the subject is exposed to the stimulus or after the subject is exposed to the stimulus. For example, the questionnaire can include a graphic or verbal character scale that combines the three emotional dimensions of pleasure, arousal, and dominance into a score.

The stimulus can be in any form or forms, such as those selected from the group consisting of visual, auditory, tactile, olfactory, and taste. In one embodiment, the stimulus is a marketing communication. For example, the marketing communication can be an advertisement or the concept for an advertisement. In one embodiment, the marketing communication is selected from the group consisting of product or service attribute, product or service benefit, brand, logo, tag line, packaging, and music. In one embodiment, the stimulus is a product or service that the subject experiences using one or more senses. In another embodiment, the stimulus is a representation of an environment, situation, behavior, or a combination of two or more of the foregoing. In another embodiment, the stimulus is a speech or lecture (e.g., a political speech). In one embodiment, the stimulus is an image, video, or live performance. In one embodiment, the stimulus is an attorney's and/or witness's potential communication before a judicial authority and/or jury.

In the methods and system of the invention, prior to exposing the subject to the stimulus, the subject can be selected from a group of individuals based on one or more pre-defined parameters. For example, the parameter can be one or more selected from the group consisting of age, income, gender, education, occupation, race, nationality, political affiliation, sexual orientation, height, weight, health, mental or physical disease state, injury, addiction, level of daily or weekly exercise, and geographical domicile. In this way, classes of individuals predisposed to a given type of emotion response to a given type of stimulus can be determined.

In the methods and system of the invention, monitoring with the brain imaging device can be carried out before, during, and/or after exposure to the stimulus. The subject can comprise a single individual or a plurality of subjects. In one embodiment, monitoring with the brain imaging device comprises determining which of the subject's brain regions exhibit activity in response to the stimulus. In another embodiment, monitoring with the brain image device comprises determining which of the subject's brain regions exhibit discrete dimensional activity.

In another embodiment, monitoring with the brain image device comprises determining which of the subject's brain regions exhibit increased activity in response to the stimulus, and wherein the method further comprises comparing the brain region or brain regions determined to exhibit increased activity with a brain region or brain regions in the same subject or a different subject determined to exhibit increased activity in response to the same stimulus or a different stimulus. Optionally, the stimulus can be based on the outcome of the comparison. In one embodiment, the emotional response score is a pleasure, arousal, and dominance (PAD) score, and the monitoring comprises determining which of the subject's brain regions exhibit discrete dimensional activity.

Optionally, the methods of the invention can further comprise comparing the subject's emotional response score, the brain imaging data and/or the relationship there between, to a reference emotional response score, reference brain imaging data, and/or a reference relationship between a reference emotional response score and reference brain imaging data (e.g., a control or other score, data, and/or relationship).

As indicated above, another aspect of the invention is a method for identifying an emotional response to a stimulus, comprising exposing a subject to a stimulus; monitoring the subject with a brain imaging device to obtain brain imaging data; and determining the subject's emotional response score for the stimulus based on the brain imaging data. In one embodiment, the emotional response score is a pleasure, arousal, and/or dominance (PAD) score, and the subject's emotional response score is based on the location and intensity of brain activity. As indicated above, the brain imaging device is preferably a functional magnetic resonance imaging (fMRI) device, but other functional brain imaging devices can be used. In one embodiment, the stimulus is in one or more forms selected from the group consisting of visual, auditory, tactile, olfactory, and taste. In one embodiment, the stimulus is a marketing communication. As indicated above, monitoring with the brain imaging device can carried out before, during, and/or after said exposing. In one embodiment, the emotional response score comprises a score for the dimension of pleasure based on the extent of brain activity in the inferior frontal gyms (left and/or right sides) and/or middle temporal gyms (left and/or right sides); or a score for the dimension of arousal based on the extent of brain activity in the right middle frontal gyms and/or left middle occipital gyrus; or both. The method of the invention can further comprise presenting the determined emotional response score to the subject, a client, or other recipient as a deliverable, such as a perceptual map and/or text analysis. The method of the invention can further comprise comparing the determined emotional response score to a reference emotional response score, such as a control, from the same subject, from a different or similar subject, from a group of subjects.

Another aspect of the invention comprises a system for correlating an emotional response score with brain imaging data, or for identifying an emotional response to a stimulus, comprising a brain imaging device, a computer, and a subject interface for surveying a subject to determine the subject's emotional response score to a stimulus, wherein the brain imaging device, computer, and subject interface are in direct or indirect operable communication. In one embodiment, the interface is a keyboard or touch screen in physical or remote communication with said computer. Preferably, the interface is a keyboard within the brain imaging device. Preferably, the brain imaging device is a functional magnetic resonance imaging (fMRI) device, but other functional brain imaging devices can be used. The system can further comprise a device for presenting the stimulus to the subject, such as a video screen, and/or speakers or headphones (or other noise emitters), and/or scent emitter (e.g., an atomizer for perfumes).

One embodiment of the invention is a method for identifying an emotional response to a stimulus, comprising exposing a selected subject to a stimulus; monitoring the subject with a functional brain imaging device, such as an fMRI device or a positron emission tomography (PET) device, while exposing the subject to the stimulus; collecting data from the brain imaging device; providing the subject with a questionnaire to determine the subject's emotional response score, wherein the questionnaire is completed by the subject; and correlating the data from the questionnaire with the data from the brain imaging device. Preferably, the questionnaire is an AdSAM® questionnaire. The subject can be provided with the questionnaire, and can complete the questionnaire, while the subject is being exposed to the stimulus or after the subject is exposed to the stimulus. The subject can be provided with the questionnaire, and can complete the questionnaire, while the subject is being monitored with the brain imaging device or after the subject is monitored with the brain imaging device. The questionnaire can be filled out by the subject after each scan with the functional brain imaging device, or after each series of scans, for example.

The brain imaging device allows the researcher to assess which region or regions of the brain are relatively active while a subject is exposed to the stimulus. Preferably, the subject is exposed to multiple stimuli (such as multiple commercials) while being monitored with the functional brain imaging device.

In the methods and system of the invention, the stimulus to which the subject is exposed can be of a form such as visual, auditory, tactile, olfactory, taste, or a combination or two or more of the foregoing. In one embodiment, the stimulus is a media communication such as a marketing communication. For example, the stimulus can be a product or service concept, advertising (concept and/or finished ads), product or service attributes, product or service benefits, brands, logos, tag lines, packaging, music (such as a theme song or jingle), etc. In one embodiment, the stimulus is a full-length video advertisement, or a portion thereof. For example, the stimulus can be a movie trailer or advertisement for a television show. In another embodiment, the stimulus is the scent of a perfume or cologne.

In another embodiment, the stimulus is a description of an environment, situation, behavior, or a combination of two or more of the foregoing. For example, the stimulus can be a description of a hypothetical environment, description of an actual environment, description of a hypothetical situation, description of an actual situation, description of hypothetical behavior, or a description of an actual behavior.

Optionally, in any of the embodiments, the method of the invention can further comprise selecting the subject from a group of individuals based on one or more predefined parameters such as age, income level, gender, education, occupation, race, sexual orientation, height, weight, health, geographic domicile, etc. Results obtained from a subject can be compared to the results obtained from individuals that are the same, similar, or different with respect to one or more predefined parameters, such as age, income level, gender, education, occupation, race, nationality, political affiliation, sexual orientation, height, weight, health, geographic domicile, etc.

A single subject can be tested, or a group of two or more subjects can be tested simultaneously or sequentially. Optionally, a group of subjects can be exposed to the same stimulus simultaneously or sequentially. Subjects in a group can be the same, similar, or different with respect to one or more predefined parameters, such as age, income level, gender, education, occupation, race, nationality, political affiliation, sexual orientation, height, weight, health, level of daily or weekly exercise, geographic domicile, etc.

Optionally, responses to the questionnaire can be timed, and the latencies can also be used as part of the analysis.

Optionally, the method of the invention further comprises monitoring the subject's behavior for a predetermined time period after exposing the subject to the stimulus.

Optionally, methods known in the art for verifying that a subject is fully immersed in the stimuli (i.e., paying attention to the stimuli) can be used.

Optionally, the results from one subject can be compared with the results of another subject. Likewise, the results of a set of subjects can be compared with the results of another set of subjects. There are no limits to the numbers of subjects, and sets of subjects, that can be compared. In one embodiment, the method comprises exposing a first set of subjects to a stimulus; monitoring the first set of subjects with a functional brain imaging device, such as an fMRI device, while exposing the first set of subjects to the stimulus; collecting data from the brain imaging device; providing the first set of subjects with a questionnaire (e.g., an AdSAM® questionnaire) to determine the first set of subjects' emotional response scores, wherein the questionnaire is completed by the subjects; correlating the data from the questionnaire with the data from the brain imaging device; exposing a second set of subjects to a stimulus, wherein the stimulus is the same or different from that exposed to the first set of subjects; monitoring the second set of subjects with the functional brain imaging device, while exposing the second set of subjects to the stimulus; collecting data from the brain imaging device; providing the second set of subjects with a questionnaire to determine the second set of subjects' emotional response scores, wherein the questionnaire is completed by the second set of subjects; correlating the data from the questionnaire with the data from the brain imaging device; and comparing the emotional response scores and/or activated brain regions of the first set of subjects to the emotion response scores and/or activated brain regions of the second set of subjects. In those instances where the first set of subjects is exposed to a different stimulus than that of the second set of subjects, the method can further comprise analyzing the characteristics of the first stimulus and the second stimulus (comparing them) to determine if there is a correlation between a stimulus characteristic and an emotional response and/or activated brain region. Optionally, the first set of subjects and the second set of subjects can be selected based on similarities or differences in one or more predefined parameters, such as age, income level, gender, education, occupation, race, nationality, political affiliation, sexual orientation, height, weight, health, geographic domicile, etc.

The method of the present invention can be used to measure the emotional response to any situation or stimuli, and can involve one or more senses such as visual, auditory, tactile, olfactory, taste, etc. For example, in marketing communication research, the emotional response data can be determined for such things as product or service concepts, advertising (concept and/or finished ads), product or service attributes, product or service benefits, brands, logos, tag lines, packaging, music, etc. The method of the invention can also be used to assess emotional response to different purchase options (e.g., retail vs. online), lifestyle issues, product usage situations, and other scenarios. In personnel management studies, the method of the invention can be used to measure employee satisfaction or employee morale. For example, the method of the invention can be used to assess how employees feel in a particular work environment (situation).

Using the methods of the present invention, emotional segmentation can be determined to assess the difference between audience segments and evaluate their feelings about such things as political issues, shopping habits, health concerns, changing lifestyles, basic values, and environmental concerns. For example, the subject can be exposed to real or hypothetical situations, or descriptions thereof, while monitoring the subject with a functional brain imaging device. The situation can be presented to the subject in any medium, e.g., performed live, either or remotely or in the subject's presence, as a printed document (either hard copy or electronic copy displayed on a monitor, for example), described verbally, or any combination of the foregoing. The methods of the invention can be used to evaluate feelings evoked by advertisements in relationship to feelings about the brands.

At specified periods after scanning with the functional brain imaging device (for example, ranging from one day to several months), the subject can be tested for his or her memory and feelings about the stimulus. This is particularly useful when the stimulus is marketing information because it is the advertisers' goal to provide consumers with ads they will remember that include information on the advertisers' product or service.

The data obtained from the functional brain imaging device is compared to the results of the questionnaire to obtain a correlation. The correlation reveals the brain areas (particular brain region or sets of regions) of relative activation during monitoring, in which the amount of brain activation during exposure to the stimulus predicts later behavior. For example, the present inventors have determined that activation of the inferior frontal gyrus (left and right sides of the brain) and the middle temporal gyrus (left and right sides of the brain) correlate with pleasure. Furthermore, the right middle frontal gyms and left middle occipital gyms correlate with arousal.

Once specific brain structures are identified as correlating with a certain stimuli (or type of stimuli) and emotional response score (e.g., PAD score), other stimuli can be developed and tailored, using the results of the invention to predict future behavior and/or preferences in a particular subject or category of subjects (such as similarly situated subjects). For example, results can be used to predict future behavior with respect to purchase or consumption of products or services.

Using the method of the invention, emotional abnormalities and corresponding therapeutic interventions can be studied. Once specific brain structures are identified as correlating with a certain type of stimuli and emotional response score (e.g., PAD score), therapeutic interventions (e.g., pharmacological and/or psychosocial interventions) that will increase or decrease activation of the implicated brain structures (and downstream mechanisms under their control) can be developed.

AdSAM®

AdSAM® uses a nonverbal, cross-cultural, visual measure of emotional response based on the pleasure, arousal, and dominance (PAD) theory of emotion. The measure consists of a graphic character arrayed along three different scales: pleasure (measures the positive/negative aspect of the feeling), arousal (measures the level of intensity or involvement in the feeling) and dominance (measures the degree of empowerment the respondent feels). The measure taps into the core of the human emotional reactions around the globe.

AdSAM® was developed using the visual affective measure SAM, the Self-Assessment Maniken (Lang, P. J. (1980) "Behavioral treatment and bio-behavioral assessment: Computer applications" In J. B. Sidowski, J. H. Johnson & T. A. Williams (Eds.), Technology in mental health care delivery systems (pp. 119-137), Norwood, N.J.: Ablex), which is incorporated herein by reference in its entirety. SAM is the visual measurement of the three dimensions of pleasure, arousal, and dominance. This approach adequately describes the full spectrum of human emotions in three independent bipolar dimensions. They are: P-pleasure/displeasure, A-arousal/non-arousal, and D-dominance/submissiveness. Pleasure/displeasure ranges from extreme happiness to extreme unhappiness. Arousal/non-arousal represents a continuum ranging from a level of physical activity, mental alertness or frenzied excitement, to inactivity, mental inalertness, or sleep. Dominance/submissiveness refers to a feeling of total power and control or influence versus the inability to influence a situation or a feeling of lack of control. Evidence shows that these three dimensions are reliably measured and alone are sufficient to define all emotional states (Mehrabian and Russell (1977) *Journal of Research in Personality,* 11:273-294), which is incorporated herein by reference in its entirety. Sam contains three graphic scales, each of which represents one dimension of the Mehrabian and Russell's PAD paradigm (Lang, P. J. (1980) "Behavioral treatment and bio-behavioral assessment: Computer applications" In J. B. Sidowski, J. H. Johnson & T. A. Williams (Eds.), *Technology in mental health care delivery systems* (pp. 119-137), Norwood, N.J.: Ablex; Morris, J. D. (1995) *Journal of Advertising Research,* 35(6):63-68; which is incorporated herein by reference in its entirety).

SAM depicts each PAD dimension with a graphic character arrayed along a continuous nine-point scale. For pleasure, SAM ranges from a smiling, happy figure to a frowning, unhappy figure; for arousal, SAM ranges from sleepy with eyes closed to excited with eyes open. The dominance scale shows SAM ranging from a very small figure representing a feeling of being controlled or a submissive to a very large figure representing in-control or a powerful feeling. SAM has been used in numerous psycho-physiological studies since its development. The correlations between scores obtained using SAM and those obtained from Mehrabian and Russell's semantic differential procedure were impressive for both pleasure and arousal and smaller but still substantial for dominance (Lang, P. J. (1985) "The Cognitive Psychophysiology of Emotion: Anxiety and the Anxiety Disorders" Hillsdale, N.J.: Lawrence Erlbaum, which is incorporated herein by reference in its entirety). It is clear that visually oriented scales using a graphic character eliminate the majority of problems associated with verbal measures or nonverbal measures that are based on human photographs. In addition, subjects can complete ratings on the SAM scales in less than 15 seconds, allowing numerous stimuli to be tested in a short amount of time and causing less respondent wear out than on the verbal measures. Subjects have expressed greater interest in SAM ratings versus verbal self-reports in a number of studies and have stated that SAM is more likely to hold their attention. Another advantage is that both children and adults readily identify with the SAM figure and easily understand the emotional dimensions it represents. Because SAM is a culture-free, language-free measurement it is suitable for use in different countries and cultures (Bradley M. M. et al. (1994). "Affective Picture Processing", *In the Structure of Emotion: Psycho Physiological, Cognitive, and Clinical Aspects,* N. Birbaumer and A. Ohman, eds., Toronto: Hugute-Huber, which is incorporated herein by reference in its entirety).

Following the initial, successful application of SAM in a cross-cultural environment, the need arose for a more definitive approach to evaluating advertisements. AdSAM®, the measurement tool using the method of the present invention, was developed for this purpose. AdSAM® is based upon this three dimensional model of emotion and a data set of emotion adjectives, that produce a tool for pairing emotion terms with responses to a given stimuli, such as television, radio, or internet commercials. AdSAM® provides a universal, visual measure of emotional response that eliminates the need for translation at the respondent level. Consumer responses to stimuli are matched to emotion adjectives.

As indicated above, except for the brief instructions AdSAM® requires no translation. All emotional reactions are combinations of the three core human emotions, and universal to all people. The AdSAM® measure has been used cross-culturally in over 600 proprietary worldwide studies. The AdSAM® measure eliminates verbal bias associated with commonly used adjective checklist and semantic differential scales. This measure ensures a reliable assessment of the immediate emotional response to research stimuli, bypassing rational evaluative processes.

The AdSAM® measure is rapid and easy to administer and analyze. The visual nature of the measure allows for a quick and accurate assessment of emotional response. In conjunction with the ADSAM® Diagnostic Tools, many stimuli can be assessed and analyzed in a single research setting.

Once the objectives and stimuli to be measured are established, the AdSAM® scales are easily incorporated into the study questionnaire. One set of scales is used for each stimulus question. It is recommended that the emotional response measure be the first assessment used. This ensures a more reliable measure of the immediate emotional response.

The emotional response scores (e.g., PAD scores) gathered at the time of a test are processed. The results are graphed and analyzed using the AdSAM® Diagnostic tools. The emotional response scores can be plotted on AdSAM® Perceptual Maps and can be used to analyze the overall evoked feelings, and the relative relationship of responses across stimuli and audience segments. For qualitative research, scatter plots of individual responses can be produced to analyze the degree of consistency in the individual responses.

As used herein, the emotional response score (also referred to herein as the PAD score) refers to the scores determined from data collected and processed using the AdSAM® technique. Preferably, the emotional response scores from all three dimensions (pleasure, arousal, and dominance) are determined and correlated with the functional brain imaging data. However, an emotional response score from only one or two of the three dimensions (e.g., pleasure and arousal, pleasure and dominance, or arousal and dominance) can be determined and correlated with the functional brain imaging data.

In quantitative research, AdSAM® Emotion Groups are used to assess the degree of consistency in the overall responses and to identify potential emotional segments. Relationships between the emotional responses and other questions are compared with correlation analyses. The emotional response data is also cross-tabbed with persuasion scores to assess the impact of the emotional response on persuasion.

Functional Magnetic Resonance Imaging

Preferably, the functional brain imaging device used to carry out the method of the invention is an fMRI device. Image intensity observed in MR images is determined by various tissue contrast mechanisms: proton density, T1 and T2 relaxation rates, diffusive processes of proton spin dephasing, loss of proton phase coherence due to tissue magnetic susceptibility variations and in-flow of blood plasma protons. Two dominant tissue contrast mechanisms have functional sensitivity in MR imaging and are produced via hemodynamic responses. Precise changes in brain activation or metabolism are not directly observed, but the effects of local increases in blood flow and microvascular oxygenation on one or more of the aforementioned MR mechanisms can be mapped as a change in raw image intensity.

One mechanism depends upon the fact that the microvascular MR signal on T2 and T2* weighted images is strongly influenced by the oxygenation state of the blood. The rate of loss of proton spin phase coherence is a measure of T2 and local magnetic field homogeneity (T2*); this can be modulated by the presence of intravoxel deoxyhaemoglobin. Recent data shows that the observed T2* is dependent on the presence of blood deoxygenation and that deoxygenated haemoglobin is a "blood oxygenation level dependent" or "BOLD" effect that can be observed by noninvasive MR imaging at high magnetic fields.

The BOLD imaging technique does not measure tissue perfusion or flow directly, however, because over 70% of the brain's blood lies within the microvascular capillaries and venules, the measurement of the magnetic susceptibility-induced T2* signal loss is thought to most reflect the regional deoxyenation state of the venous system. In addition, proton perfusion and diffusion through changing local gradients modulated by changing oxy-/deoxyhaemoglobin levels has a direct impact on the observed T2 relaxation times, which is another mechanism of tissue contrast generation. Amongst these various mechanisms, the T2* effect is larger by factors of 3 to 10 and is the dominant and most widely-studied mechanism employed in fMRI.

The response to a local increase in metabolic rate is increased delivery of blood to the activated region. Such a change in haemodynamics produces small alterations in T1, T2 or T2*, which can be visualized as a change in MR image intensity (approx. 1-10%).

A basal state correlates with normal blood flow, basal Hbr level, basal cerebral blood volume (CBV), and normal MRI signal. An activated state correlates with increased blood flow, decreased Hbr level (due to lower field gradients around the vessels), increased CBV, and increased MRI signal (from lower field gradients).

A description of the fMRI technique can be found in U.S. Pat. No. 6,099,319, filed Nov. 9, 1998, which is incorporated herein by reference in its entirety. The subject in a typical experiment will be exposed to the magnet (e.g., lie in the magnet) and be exposed to one or more stimuli. For example, the subject can wear special glasses or goggles so that images can be shown during the experiment. Next, MRI images of the subject's brain are developed. Typically, a high resolution single scan is initially taken. This is used later as a background for highlighting the brain areas that were activated by the stimulus. Next, a series of low resolution scans are taken over time, for example, 150 scans, one every 5 seconds. For some of these scans, the stimulus will be presented, and for some of the scans, the stimulus will be absent. The low resolution brain images in the two cases can be compared, to see which parts of the brain were activated by the stimulus.

After the experiment has finished, the set of images is analyzed. First, the raw input images from the MRI scanner require mathematical transformation (e.g., Fourier transformation, a spatial "inversion") to reconstruct the images into "real space", so that the images appear as brains. The rest of the analysis is done using a series of tools that correct for distortions in the images, remove the effect of the subject moving their head during the experiment, and compare the low resolution images taken when the stimulus was absent (e.g., off) with those taken when it was present (e.g., on). Typically, the final statistical image shows up bright in those parts of the brain that were activated by the stimulus. These activated areas are then shown as colored regions on top of the original high resolution scan, for interpretation of the experiment. This combined activation image can be rendered in 3-D, and the rendering can be calculated from any angle.

Positron Emission Tomography

PET is the tomographic imaging of local metabolic and physiologic functions in tissues, the images being formed by computer synthesis of data transmitted by positron-emitting radio nuclides, often incorporated into natural biochemical substances and administered to the subject. A computer traces the path of photons and produces a composite image representing the metabolism level of the tissue.

A description of the PET technique can be found in U.S. Pat. No. 6,099,319, filed Nov. 9, 1998, which is incorporated herein by reference herein in its entirety. Typically, during a PET scan, the subject inhales or is otherwise administered a trace amount of radioactive oxygen, radioactive carbon, or a radioactive form of glucose, while the subject is engaged in the physiological task (in this case, while the subject is exposed to a stimulus, such as media information). The radioactive tracer travels through the circulatory system, and into the brain. The more active a part of the brain is during the task, the more blood and blood-born products are delivered to that area. Hence, more radioactively tagged tracer materials are present in areas that were more active while the task was being performed. The PET scanner is equipped with a series of radiation detectors that quantify the level of radiation in a 3-D space. After the scan is completed, the information from the PET scanner is analyzed by a program that maps the region-specific levels of radiation onto the topology of the brain. The result is an image of the brain that depicts the differential blood flow during the performance of the task and a set of statistical values that indicate the significance of the blood flow to each region.

Unlike previous fMRI (functional MRI) emotion research that focused on either locating specific emotions in the brain or linked the emotional response to an external behavior, the study described in the Example searched brain regions to validate a three-dimensional construct, namely pleasure, arousal and dominance or PAD, of emotional response to marketing communication. Emotional responses to five television commercials were measured with AdSAM (Self-AssessmentManikins) for PAD, and fMRI. The AdSAM responses were analyzed and showed significant differences on pleasure and arousal among the stimuli. These differences were investigated with fMRI, identifying patterns of BOLD signals. Bilateral changes of BOLD signals in the inferior frontal gyri and middle temporal gyri were associated with the difference on pleasure. Changes of BOLD signals in the right superior temporal gyms and right middle frontal gyrus were associated with the difference on arousal. The findings suggest a dimensional process of emotional response detection in the brain.

Following is an example that illustrates materials, methods, and procedures for practicing the invention. The example is illustrative and should not be construed as limiting.

Materials and Methods

Subjects. Twelve healthy, right-handed adult participants (6 males/6 females, age range 22-28, mean age 24.8) signed written, informed consent for the protocol approved by the Institutional Review Board at the University of Florida. At the time of the scan, none of the participants reported taking any psychiatric medication or having any history of neurological disorders. All of the participants stated having either normal vision or corrected to normal vision, and three of the participants used specialized, non-magnetic corrective lenses inside the scanner. All participants were financially compensated $50.00 USD.

Experimental Protocols. The subjects viewed five commercials inside of the scanner in a block design paradigm created with E-Prime (Psychology Software Tools, Pittsburgh, Pa.). The commercials were presented by back-projection using a 17" LCD screen with a resolution of 1024 pixels by 768 pixels through the Integrated Functional Imaging System (IFIS, MRI Devices, Inc., Waukesha, Wis.). An MRI-compatible auditory system (Resonance Technology, Inc.) with stereo earphones and a microphone protected participants from scanner noise while permitting verbal communication with the operator and transmitted the sound of the commercials. The first two commercials lasted 30 seconds each and the other three commercials lasted 1 minute each. Resting blocks consisting of viewing a red cross on a black screen for durations of 30 seconds were interspersed between each commercial block.

The functional paradigm consisted of six runs with each run except for the initial run being separated into three blocks: 1) a resting period, 2) a commercial, and 3) the AdSAM® task. The first run started with a 30 second resting block and then included two sets of the AdSAM® task in response to "How do you normally feel?" and "How do you feel right now?". The first two commercials lasted 30 seconds each and the other three commercials lasted 1 minute each. Resting blocks consisted of viewing a red cross on a black screen for thirty seconds and were interspersed between each commercial block. The AdSAM® task consisted of three trials that rated pleasure, arousal, and dominance. The participants viewed the resting state red cross hair for the remainder of the 45 second block after completing the trials.

After watching each commercial, the participants were asked to convey their feelings in terms of pleasure (happy vs. sad), arousal (stimulated vs. bored), and dominance (in control vs. cared for) by selecting the most appropriate Self-Assessment Manikin out of five possible choices. The responses and reaction times were recorded with a right-handed button response glove (IFIS, MRI Devices, Inc., Waukesha, Wis.). The participants were instructed to indicate how they felt after watching each commercial by rating the AdSAM® scales without spending a lot of time thinking about the questions. They were explained how to best interpret the manikin figures. Outside of the scanner, they practiced the task by answering questions regarding their general feelings and their feeling towards a commercial for V8 vegetable juice.

Data Analysis. BrainVoyager v. 4.9.6 (Brain Innovations, Maastricht, Holland) was used to analyze all of the imaging data. The functional images from each participant were first co-registered with the 3D anatomic images and then normalized into Talairach space. The resulting 3D functional data then underwent motion correction, linear trend removal, spatial smoothing (5.7 mm FWHM Gaussian filter). A general linear model (GLM) produced voxel-wise statistical activation maps. The predictors were estimated hemodynamic responses to the tasks. Contrasts between the predictors were used to evaluate the relative contribution of each condition to the variance in the BOLD signal. A statistical threshold was set to $p<0.052$ corrected with a minimum cluster size of 150 voxels when comparing the BOLD signal between the tasks. ROI's were analyzed for selected clusters of significantly activated voxels. Within each ROI, the BOLD responses for each condition were visualized using time-locked averaging of the percentage signal change relative to the baseline resting condition.

Imaging Parameters. A 3T head-dedicated MRI scanner (Siemens Allegra; Munich, Germany) was used. The functional data were overlaid onto T1-weighted 3D anatomical images that were acquired with a MPRAGE sequence in the following parameters: Matrix=256×256, TR=1.5 s, TE=4.38 ms, FA=8°, FOV=240 mm, 160 slices, slice thickness=1.1 mm. Functional images were acquired with a gradient-echo EPI sequence sensitive to the BOLD signal in the following parameters: Matrix=64×64, TR=3.0 s, TE=30 ms, FA=90°, FOV=240 mm, 36 slices, slice thickness=3.8 mm without gaps. The first two functional volumes were discarded because of their T1 saturation and no task was performed during this period.

EXAMPLE

Evaluation of Emotional Response to Commercials

The current study was designed to assess the validity of the dimensional approach for measuring emotional response by comparing the responses to those obtained through neuroimaging. The neuroimaging data was derived from blood oxygenation level dependent (BOLD) signals detected with functional magnetic resonance imaging (fMRI). The self-report data was derived from responses to the AdSAM® scale (Morris, J. D. et al. *Journal of Targeting, Measurement & Analysis for Marketing,* 2005, 14:79-98). This scale provides a non-verbal, cross-cultural, visual measure of emotional response that measures the dimensions of pleasure, arousal, and dominance. We have been successful in using the self-report three-dimensional AdSAM technique across cultures and around the globe. We theorize that this methodology, grounded in psychological literature since the 1950's, should be the basis of emotional detection in the brain. In addition, the AdSAM version of the three dimensional process employs a non-verbal Manikin for reporting responses, and therefore is a better tool than a verbal technique that requires respondents to cognitively translate their reactions into words before reporting their feelings.

The neuroimaging targeted the amygdala, prefrontal cortex, and temporal cortex for several reasons. First, the prefrontal cortex has been found to have neural projections to the amygdale (McDonald, A. J. et al. *Neuroscience,* 1996, 71:55-75), and the temporal cortex has been found to send stimulus information to the prefrontal cortex (Hasselmo, M. E. et al. *Behavioral Brain Research*, 1989, 32:203-218). Second, the temporal cortex has been found to allow the brain to merge perceptual and semantic information, past memories and short-term manipulation of the stimuli (Mitchell, R. L. C. et al. *Neuropsychologia*, 2003, 41:1410-1421). Third, both the semantic information and the dynamic nature of video clips have been found to increase neural activity in the prefrontal cortex (Adolphs, R. *Behavioral and Cognitive Neuroscience Reviews*, 2002, 1:21-62; Decety, J. and Chaminade, T. *Neuropsychologia*, 2003, 41:127-138).

Prior to attending the scanning session, the participants completed a questionnaire that contained demographic questions. They also answered questions indicating how often they drank the targeted beverages and how often they drank the competing brands. After the scanning session, the participants completed a post-questionnaire survey indicating how many times they had previously seen the commercials and their intentions of purchasing the beverages in the future. Lastly, they had the opportunity to select one of the six drinks for their own consumption.

Figures 2A, 2B, 2C:
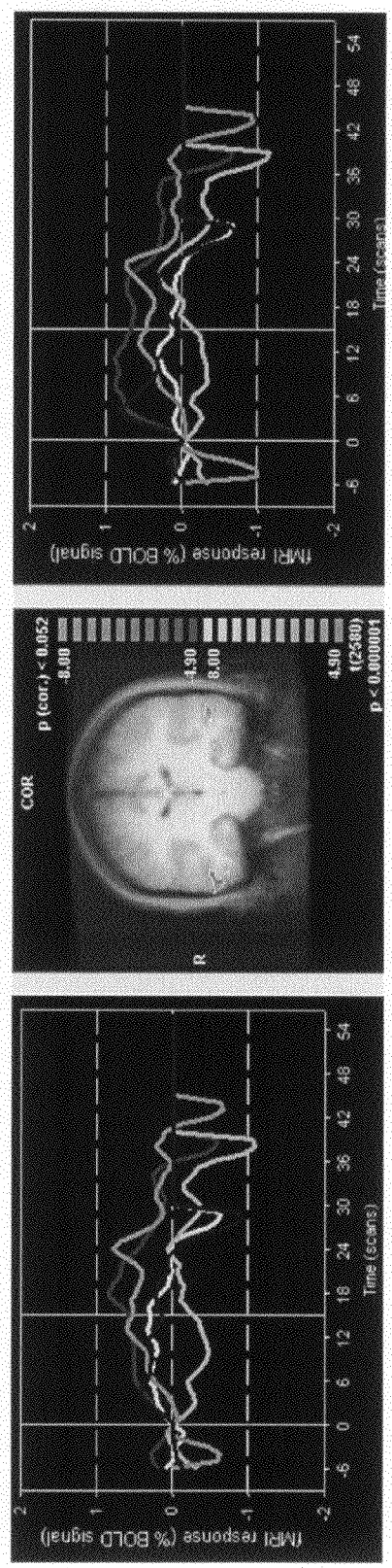
FIGS. 2A-2C are fMRI results showing bilateral activity in response to the stimulus.

Regional Dimensional Activity:

The lowest mean rating from pleasure was scored from the fur commercial, 2.7±1.1, (mn±sd) and it was significantly lower than the mean ratings from all of the other four commercials. Thus, it was decided to compare changes in BOLD (Blood Oxygen Level Dependent) signal for the combined blocks viewing the teacher, Evian®, Coke®, and Gatorade® commercials relative to the viewing of the fur commercial (4× balanced) using a strict threshold criteria of p(cor.)<0.052 and a minimum cluster size of 150 voxels. BOLD signal increases were observed in the bilateral inferior frontal gyri, BA 47, right at Tal (46,37,8) t=5.64 and left at Tal (−43,35,−4) t=5.69 (FIGS. 1A-1C) and in the bilateral middle temporal gyri, BA 21, right at Tal (59,19,12) t=5.81 and left at Tal (−55,19,−5) t=5.21 (FIGS. 2A-2C).

Figures 3A, 3B:
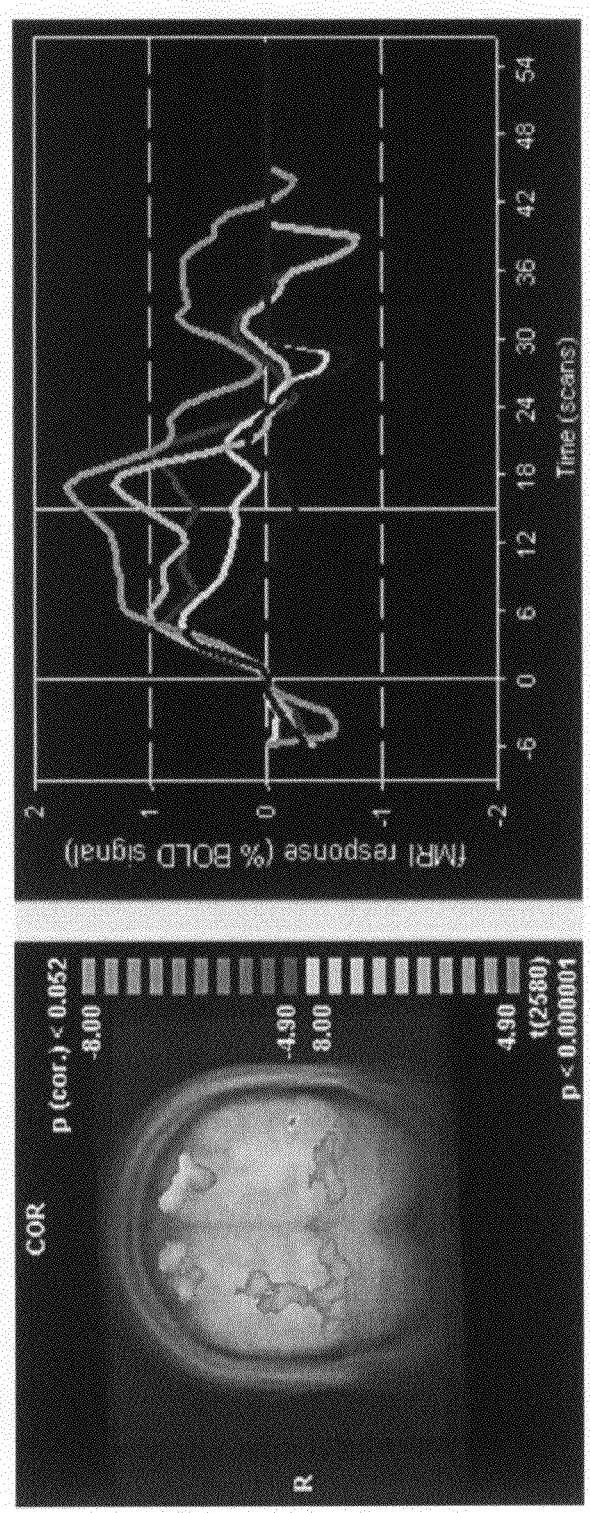
FIGS. 3A-3B are fMRI results showing brain activity in the left middle occipital gyms in response to a stimulus.
Figures 4A, 4B:
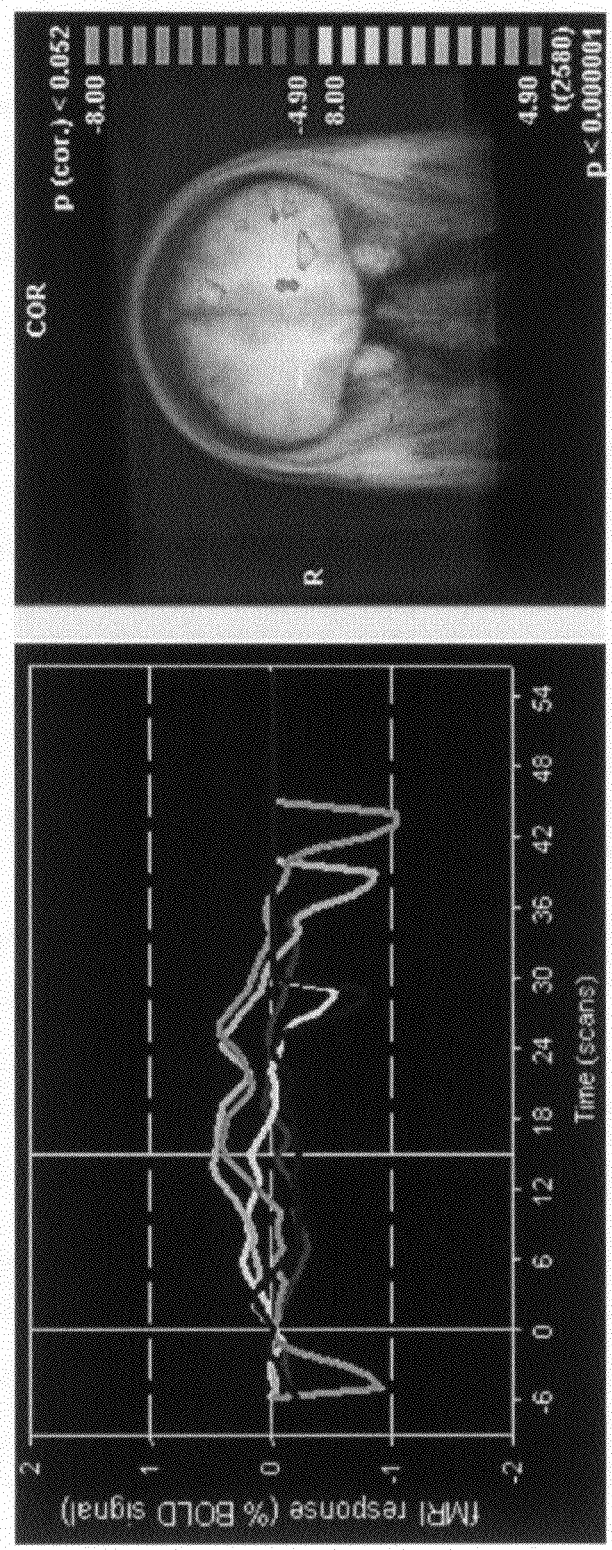
FIGS. 4A-4B are fMRI results showing brain activity in the left middle occipital gyms in response to a stimulus.

In terms of arousal, the combined scores of the Gatorade® (3.7±0.9) and fur (3.9±0.9) commercials were significantly higher than the combined scores of the Coke® (2.9±0.8) and teacher (2.9±0.6) commercials. Thus, it was decided to compare changes in BOLD (Blood Oxygen Level Dependent) signal for the Gatorade® and fur commercials relative to the viewing of the Coke® and teacher commercials using a strict threshold criteria of p(cor.)<0.052 and a minimum cluster size of 150 voxels. BOLD signal increases were observed in the left middle occipital gyms, BA 19, Tal (−46,−65,5) t=5.07 (FIGS. 3A-3B) and right middle frontal gyrus, BA 10, Tal (26,32,5) t=5.40 (FIGS. 4A-4B). The following regions were identified as exhibiting discrete dimensional activity:

Pleasure: Inferior Frontal Gyms (left & right sides) and Middle Temporal Gyrus (left & right sides).

Arousal: Right Middle Frontal Gyrus and Left Middle Occipital Gyms.

Behavioral Data

Figure 5B:
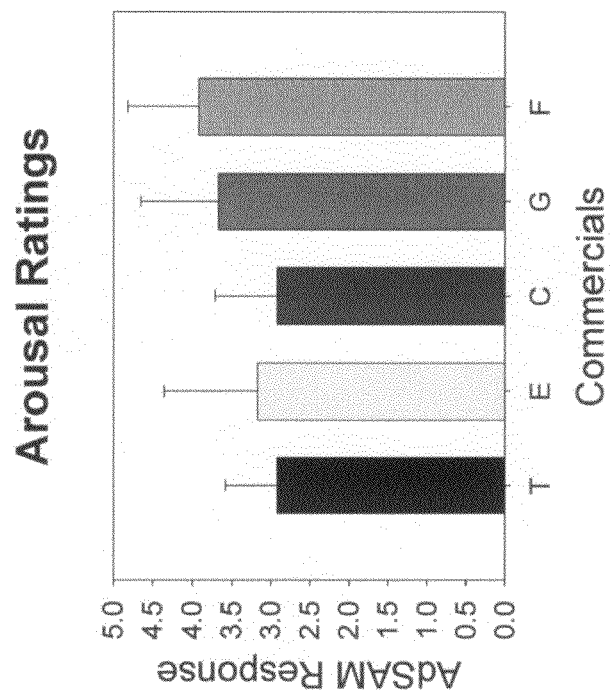
FIGS. 5A-5B show histograms of AdSAM responses for the dimensions of pleasure and arousal, respectively. In both FIGS. 5A and 5B, each of the five commercials is represented by a different color/bar (Teacher (T)=blue, Evian (E)=yellow, Coke (C)=red, Gatorade (G)=green, Anti-Fur (F)=brown).
Figure 5A:
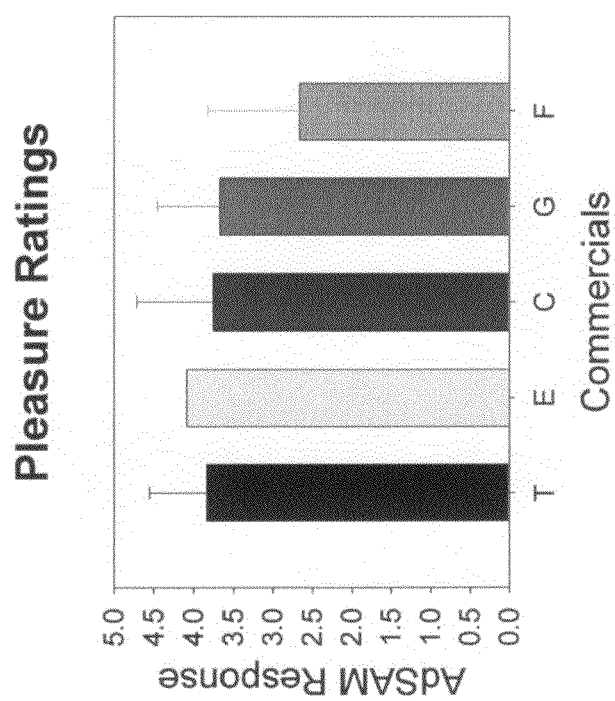
Figure 6B:
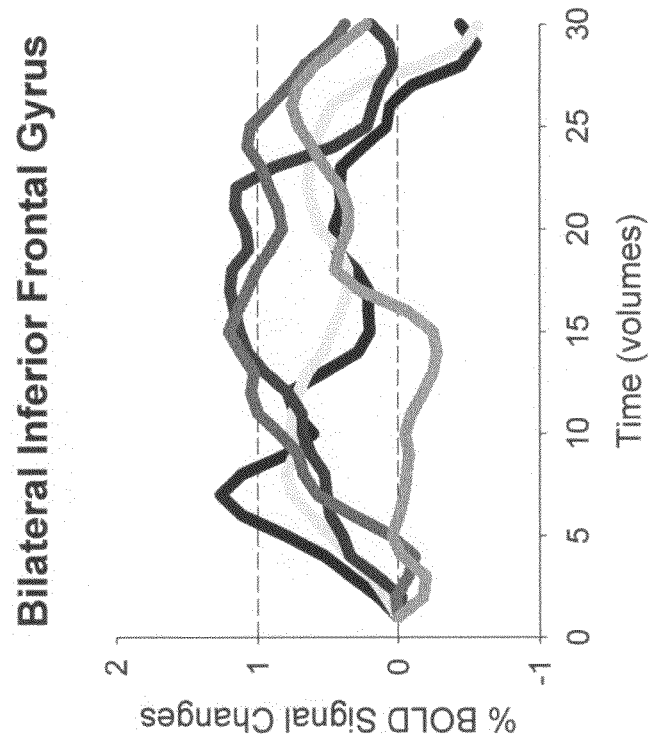
FIGS. 6A-6D illustrate contrasts between the Anti-Fur commercial (4× balanced) and the other four commercials for comparison of the pleasure dimension. The ROIs shown in FIGS. 6A and 6C include bilateral inferior frontal gyri: right at Tal (46,37,−8) t=5.64 and left at Tal (−43,35,−4) t=5.69 and the bilateral middle temporal gyri: right at Tal (59,19,12) t=5.81 and left at Tal (−55,−19,−5) t=5.21. The graphs in FIGS. 6B and 6D depict an increased BOLD signal in all four commercials relative to the Anti-Fur commercial block for the selected voxels. Each of the five commercials is represented by a different color (Teacher=blue, Evian=yellow, Coke=red, Gatorade=green, Anti-Fur=brown).
Figure 6A:
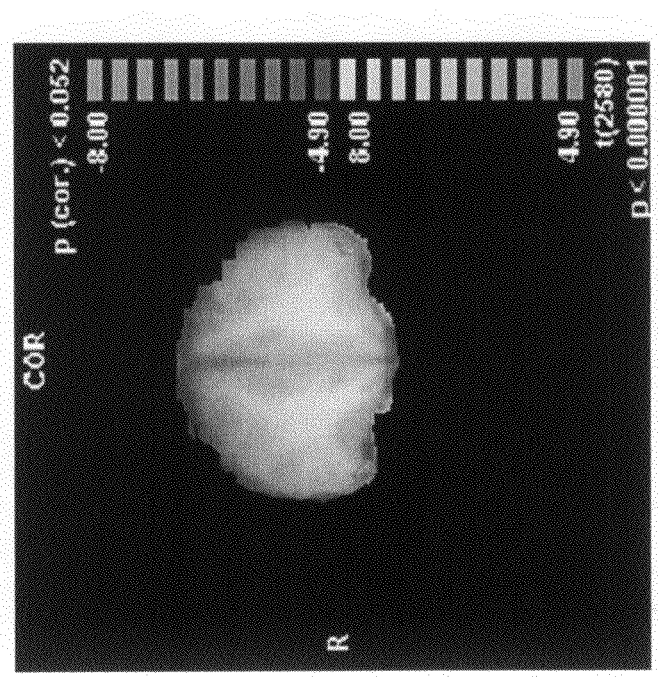
Figure 6D:
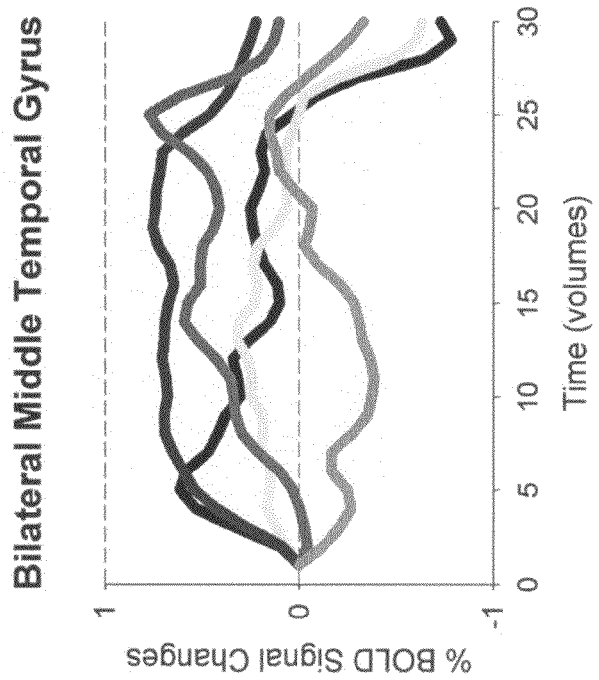
Figure 6C:
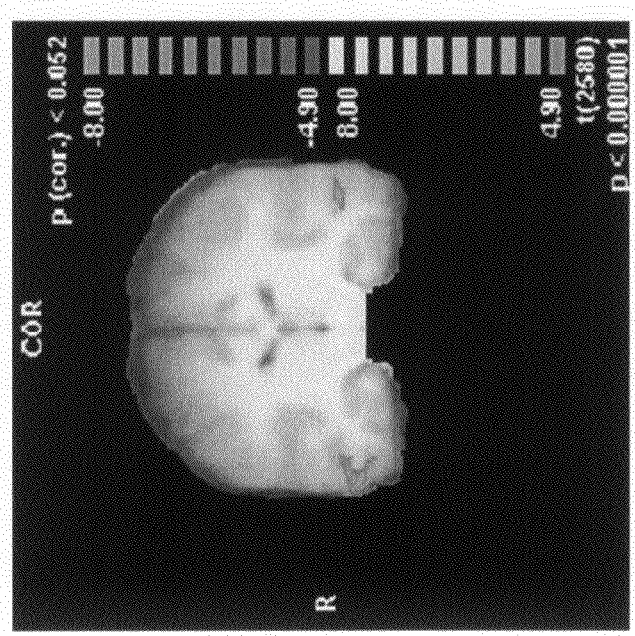

As shown in FIGS. 5A and 5B, each of the five stimuli, television commercials, was rated on a five point AdSAM® scale of Pleasure and Arousal and Dominance and was averaged from all twelve subjects (see Methods). The lowest mean rating from Pleasure was scored from the Anti-Fur commercial, 2.7±1.1, (mn±sd) and it was significantly lower than the mean ratings from all of the other four commercials (FIG. 5A). In the ratings for Arousal, the mean scores from the Anti-Fur commercial (3.9±0.9) and Gatorade commercial (3.7±0.9) were significantly higher than the scores for the Teacher commercial (2.9±0.6) and Coke commercial (2.9±0.8) (FIG. 5B). In the ratings for Dominance, the mean scores for all the five commercials did not significantly differ from one another; therefore, they are not reported.

Imaging Data

The present inventors compared changes in BOLD signal for the combined blocks viewing the Teacher, Evian, Coke, and Gatorade commercials relative to the viewing of the Anti-Fur commercial using a strict threshold criteria of p(corr.)<0.052 and a minimum cluster size of 150 voxels. BOLD signal increases were observed in the bilateral inferior frontal gyri (BA 47) and bilateral middle temporal gyri (BA 21) and BOLD signal decreases in the right superior Pparietal lobe (Table 1).

There were three steps in the selection of regions of interest (ROIs) in the Pleasure dimension from Table 1. First, beta weights were acquired with the above-mentioned general linear model (GLM) on the imaging data to search for significantly activated regions, which are listed in Table 1. Beta weights are estimates of the hemodynamic responses to the modeled condition. Second, the beta weights were contrasted to the behavioral data collected through AdSAM® to examine the correspondence between the two types of measures. Third, the time locked average response plots of significantly activated regions were used to identify ROIs where the patterns of activations also highly corresponded to the pattern of the AdSAM® behavioral data for the pleasure dimension. By following those three steps, the present inventors selected to present the bilateral inferior frontal gyri and bilateral middle temporal gyri in FIGS. 6A-6D for the pleasure dimension.

Changes in BOLD signal for the combined blocks of the Anti-Fur and Gatorade commercials were also compared relative to the viewing of the Teacher and Coke commercials using the same strict threshold criteria of p(corr.)<0.052 and a minimum cluster size of 150 voxels. Several BOLD signal increases were observed in the left hemisphere regions including the middle frontal gyrus (BA9), superior frontal gyrus (BA10), middle occipital gyms (BA19), inferior temporal gyms (BA37) and thalamus, and in the right hemisphere regions including the cerebellum, middle frontal gyrus (BA10), and optic radii (Table 2).

Figure 7C:
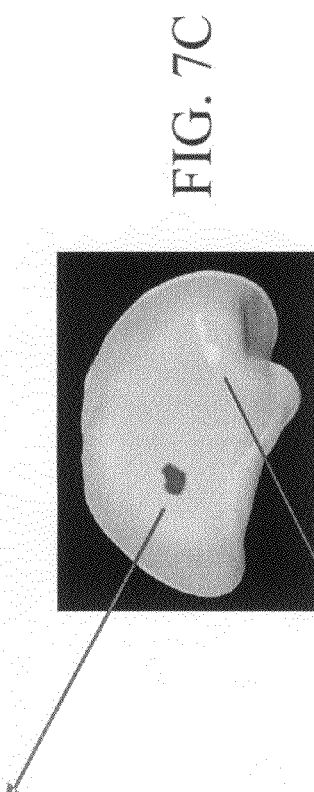
FIGS. 7A-7C illustrate contrasts between the Gatorade and Anti-Fur commercials and the Teacher and Coke commercials. The ROIs shown include the right superior temporal gyms: at Tal (64,−37,14) t=5.69 and the right middle frontal gyms: at Tal (26,32,5) t=5.40 (FIG. 7C). The graphs in FIGS. 7A and 7B depict an increased BOLD signal in the blocks containing the Gatorade and Anti-Fur commercials relative to the blocks containing the Teacher and Coke commercials for the selected voxels.
Figure 7A:
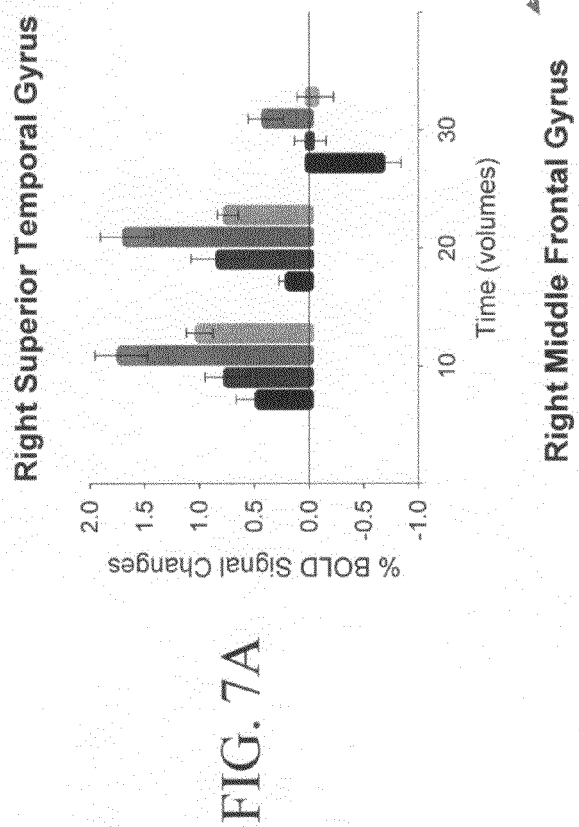
Figure 7B:
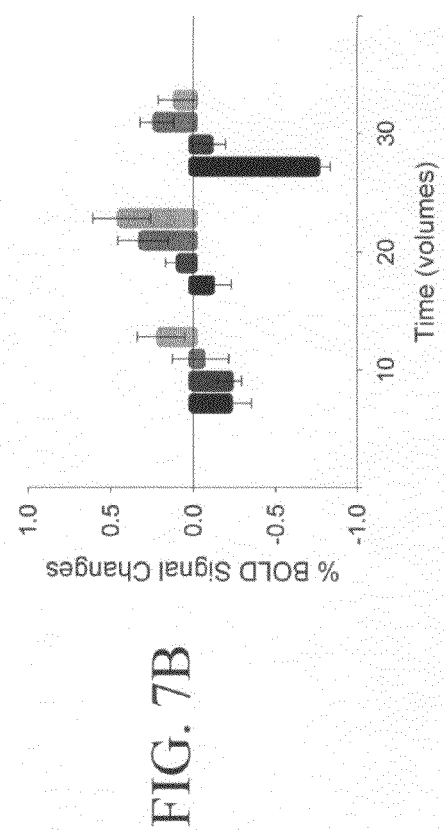

Again, the above-mentioned three steps were used to select ROI's for the arousal dimension and present the right middle frontal gyms and right superior temporal gyrus in FIGS. 7A-7C. As shown in the figure, the time locked average responses in these ROI's corresponded well to the AdSAM® behavioral data of arousal.

In this study, the present inventors evaluated emotional reactions based upon our hypotheses that AdSAM and PAD ratings are related to brain response because the PAD process is duplicated in actual brain function. The empirical evidence supported the identification of regions of the brain that correspond to both the pleasure-displeasure and arousal-calm dimensions of the PAD model of emotions (Russell, J. A., and Mehrabian, A. *Journal of Research in Personality*, 1977, 11:273-294). Further, the self-report data generated through the AdSAM® measure correlated well with the fMRI data.

The AdSAM® pleasure scores of four stimuli (Teacher, Evian, Coke and Gatorade) were significantly higher than that of the Anti-Fur commercial (FIGS. 5A-5B). The disturbing content of the Anti-Fur Commercial that included a scene showering blood most likely contributed to this intense unpleasant emotion. When the imaging data of the first four commercials were contrasted to those of the Anti-Fur commercial, significant differences were identified in brain regions that are known to be associated with emotional valence. These regions include the bilateral inferior frontal gyrus and the bilateral middle temporal gyms (FIGS. 6A-6D) which have been found to be associated with emotional responses (George, M. S. et al. *Archives of Neurology*, 1996, 53:665-670; Sprengelmeyer, R. et al. *Proceedings of the Royal Society of London, Series B: Biological Sciences*, 1998, 265:1927-1931). Activation in the amygdala areas is often intertwined with activation of these two areas of the prefrontal cortex (McDonald, A. J. et al. *Neuroscience*, 1996, 71:55-75); however, in this study, no significant activities were detected in the amygdala. Previous research indicates that the activation of the amygdala can be substantially reduced by an explicit request for emotional recognition (Nomura, M. et al. *Neuroscience Letters*, 2003, 348:113-116). It is possible that the activity in the amygdala was inhibited in this study because the subjects were explicitly requested to report their emotional responses leading to an inability of the stimuli to elicit strong levels of fear or anxiety related to amygdale activation (LeDoux, J. E. *Annual Review of Psychology*, 1995, 46:209-235).

The AdSAM® arousal scores of the Teacher and Coke commercials were significantly lower than those of the Gatorade and Anti-Fur commercials (FIG. 5b). When the former two were contrasted to the latter two, significant differences were identified in the right superior temporal gyrus and the right middle frontal gyms (FIGS. 7A-7C). The superior temporal gyms has been found to be a motion-processing region (Schultz, J. et al. *Neuron*, 2005, 45:625-635). Motion has been found to increase arousal (Simons, R. F. et al. *Psychophysiology*, 1999, 36:619-627); hence, the identification of motion may actually be arousal.

For dominance, there were no findings of significant differences in this data. This is not surprising since dominance often accounts for a much smaller amount of variance of emotional responses than does pleasure or arousal (Mehrabian, A., and Russell, J. A. An approach to environmental psychology, Cambridge, Mass., Oelgesschlager, Gunn and Hain, 1974) and is often not a factor in vicarious experiences such as watching a television commercial. Dominance was included in this study because it is a content feature of emotional stimuli (Bradley, M. M. and Lang, P. J. "Measuring emotion: Behavior feeling, and physiology" In Cognitive neuroscience of emotion, R. D. Lane, and L. Nadel, eds., New York, Oxford University Press, 2000, pp. 242-276). The present inventors acknowledged the theoretical importance of dominance, but primarily focused on pleasure and arousal. In future research we will attempt to manipulate dominance since it is a fundamental element of the three dimensional self-report process.

Arguably, the PAD model of emotions, as shown in these findings, appears to be a superior method for identifying the dynamics of emotional response in the brain than the discrete approach. The subjects' emotional responses were examined along the pleasure-displeasure, arousal-calm, and dominance-submissiveness dimensions and found that there were particular brain regions associated with pleasure and arousal. The discrete approach to identifying emotions has not been able to identify specific regions of the brain associated with emotional responses because it fails to eliminate the interconnectivity associated with an affective response. By focusing on patterns of responses, we were able to locate specific regions where pleasure and arousal were distinctly and significantly different from each other and where they were different among the various stimuli. This suggests that the brain evaluates external stimuli in much the way it is reported in the PAD model.

This study used a relatively small but adequate sample for fMRI studies and our findings are preliminary in nature. Further research is needed to locate the responses to the dominant dimension and to calibrate the levels of activity in the brain that distinguish among responses to stimuli. These preliminary results suggest that human emotions are dimensional and that self-report for emotional response along dimensions corresponds to specific areas of the brain:

TABLE 1

Localization of brain activation during commercials with a high level of pleasure.

| Region | BA | Side | X | Y | Z | Size | t-value |
|---|---|---|---|---|---|---|---|
| Inferior Frontal Gyrus | 47 | R | 46 | 37 | −8 | 447 | 5.64 |
| Inferior Frontal Gyrus | 47 | L | −43 | 35 | −4 | 289 | 5.69 |
| Middle Temporal Gyrus | 21 | R | 59 | −19 | −12 | 3139 | 5.81 |
| Middle Temporal Gyrus | 21 | L | −55 | −19 | −5 | 302 | 5.21 |
| Superior Parietal Lobe | 7 | R | 13 | −77 | 44 | 168 | −5.13 |

Comparison between 4 commercials (T, C, G, E) and commercial F. P(corr.) < 0.052. Only clusters >150 voxels are shown.
BA = Brodmann's Area.
Size = number of 1 $mm^3$ voxels.
X, Y, and Z refer to Talairach coordinates.

TABLE 2

Localization of brain activation during commercials with a high level of arousal.

| Region | BA | Side | X | Y | Z | Size | t-value |
|---|---|---|---|---|---|---|---|
| Cerebellum | — | R | 19 | −41 | −39 | 1629 | 5.30 |
| Inferior Temporal Gyrus | 37 | L | −48 | −43 | −11 | 1896 | 5.43 |
| Middle Frontal Gyrus | 9 | L | −36 | 28 | 30 | 477 | 5.27 |
| Middle Frontal Gyrus* | 10 | R | 26 | 32 | 5 | 1113 | 5.40 |
| Middle Occipital Gyrus | 19 | L | −46 | −65 | 5 | 159 | 5.07 |
| Pulvinar of the Thalamus | | L | −24 | −26 | 4 | 349 | 5.04 |
| Superior Frontal Gyrus | 8 | M | −7 | 29 | 47 | 2774 | 5.70 |
| Superior Frontal Gyrus | 10 | L | −16 | 44 | 10 | 214 | 5.17 |
| Superior Temporal Gyrus* | 22 | R | 64 | −37 | 14 | 808 | 5.69 |

P(corr.) < 0.052. Only clusters >150 voxels are shown.
BA = Brodmann's Area.
Size = number of 1 $mm^3$ voxels.
X, Y, and Z refer to Talairach coordinates.

Commercial Descriptions

Briefly, the first commercial consisted of a 30-second public service announcement named "Be a Hero." The commercial portrays young school children answering a question—Who is my hero? Some of them name famous people but one boy names his teachers. The narrator echoes, "Teachers have the power to change children's lives." The commercial urges those interested to get involved in teaching and make a difference.

The second commercial consisted of a 30-second advertisement for Evian water. It portrays the mountains of the French Alps, the blue sky reflecting on the natural springs, and the bright sun glimmering on the snow. It summarizes these beautiful scenes with the words on the screen, "Our factory."

The third commercial used was the classic Mean Joe Greene Coca-Cola advertisement. In this 60-second commercial, a young boy offers Mean Joe Greene of the Pittsburgh Steelers his Coke bottle in outside the locker room after a football game. At first Mean Joe Green politely declines but then changes his mind, accepts the Coke bottle, and passes his jersey to the young boy as a return gift. The commercial ends with the slogan, "Have a Coke and a smile."

The fourth commercial consisted of a 60-second advertisement for the Gatorade sports drink. With computer generated special effects, the present day 39-year-old Michael Jordan challenges the younger 23-year-old version of Michael Jordan to a game of one-on-one basketball. The older but wiser Jordan reprimands his former youthful and energetic self for not performing up to "his" potential. The commercial ends as the collegiate Michael Jordan, wearing his University of North Carolina uniform, asks to play in the next game while the other Jordans are quenching their thirst with Gatorade.

The fifth and final commercial consisted of a 60-second public service announcement condemning the use of animal Fur for clothing. It starts with scenes from a fashion show with several models showcasing Fur coats with spectators applauding and admiring them. As one model turns around, blood drips from her coat and splatters all over the spectators who are now terrified and disgusted. The commercial closes with the announcement: "It takes up to 40 dumb animals to make a Fur coat but only one to wear it."

All patents, patent applications, provisional applications, and publications referred to or cited herein are incorporated by reference in their entirety, including all figures and tables, to the extent they are not inconsistent with the explicit teachings of this specification.

It should be understood that the example and embodiments described herein are for illustrative purposes only and that various modifications or changes in light thereof will be suggested to persons skilled in the art and are to be included within the spirit and purview of this application.

We claim:

1. A method for correlating an emotional response to brain imaging data, comprising:

exposing a subject to a stimulus;

monitoring the subject with a brain imaging device to obtain brain imaging data of the subject's bilateral inferior frontal gyrus, bilateral middle temporal gyrus, right superior temporal gyrus, and right middle frontal gyrus, wherein said monitoring comprises determining which of the subject's brain regions exhibit discrete dimensional activity;

determining the subject's emotional response score for the stimulus, wherein the subject's emotional response score is determined by having the subject complete a questionnaire while the subject is exposed to the stimulus or after the subject is exposed to the stimulus, wherein the questionnaire comprises a graphic or verbal character scale that combines the three emotional dimensions of pleasure, arousal, and dominance into a score; and correlating the subject's emotional response score with the brain imaging data to determine a relationship there between, wherein said correlating comprises:

correlating the subject's emotional dimension of pleasure with the brain imaging data of the subject's bilateral inferior frontal gyrus and bilateral middle temporal gyrus; and correlating the subject's emotional dimension of arousal with the brain imaging data of the subject's right superior temporal gyrus and right middle frontal gyrus.

2. The method of claim 1, wherein the imaging device is a functional magnetic resonance imaging (fMRI) device.

3. The method of claim 1, wherein the emotional response score is a pleasure, arousal, and/or dominance (PAD) score.

4. The method of claim 1, wherein the subject's emotional response score is determined by a non-verbal measurement system.

5. The method of claim 1, wherein the subject's emotional response score is determined by a verbal measurement system.

6. The method claim 1, wherein the questionnaire comprises a graphic character scale that combines the three emotional dimensions of pleasure, arousal, and dominance into a score.

7. The method of claim 1, wherein the stimulus is in one or more forms selected from the group consisting of visual, auditory, tactile, olfactory, and taste.

8. The method of claim 1, wherein the stimulus is a marketing communication.

9. The method of claim 8, wherein the marketing communication is the concept for an advertisement.

10. The method of claim 8, wherein the marketing communication is an advertisement.

11. The method of claim 8, wherein the marketing communication is selected from the group consisting of product or service attribute, product or service benefit, brand, logo, tag line, packaging, and music.

12. The method of claim 1, wherein the stimulus is a product or service that the subject experiences using one or more senses.

13. The method of claim 1, wherein the stimulus is a representation of an environment, situation, behavior, or a combination of two or more of the foregoing.

14. The method of claim 1, wherein the stimulus is a speech or lecture.

15. The method of claim 1, wherein the stimulus is an image, video, or live performance.

16. The method of claim 1, wherein the stimulus is an attorney's and/or witness's potential communication before a judicial authority and/or jury.

17. The method of claim 1, wherein, prior to said exposing, the subject is selected from a group of individuals based on one or more pre-defined parameters.

18. The method of claim 17, wherein the parameter is selected from the group consisting of age, income, gender, education, occupation, race, nationality, political affiliation, sexual orientation, height, weight, health, level of daily or weekly exercise, and geographical domicile.

19. The method of claim 1, wherein said monitoring is carried out before, during, and/or after said exposing.

20. The method of claim 1, wherein the subject comprises a plurality of subjects.

21. The method of claim 1, wherein said method further comprises comparing the brain region or brain regions determined to exhibit increased activity with a brain region or brain regions in the same subject or a different subject determined to exhibit increased activity in response to the same stimulus or a different stimulus.

22. The method of claim 21, further comprising modifying the stimulus based on the outcome of the comparison.

23. The method of claim 1, further comprising comparing the subject's emotional response score, the brain imaging data and/or the relationship there between, to a reference emotional response score, reference brain imaging data, and/or a reference relationship between a reference emotional response score and reference brain imaging data.

* * * * *

UNITED STATES PATENT AND TRADEMARK OFFICE
CERTIFICATE OF CORRECTION

PATENT NO.      : 8,239,000 B1
APPLICATION NO. : 11/726663
DATED           : August 7, 2012
INVENTOR(S)     : Jon D. Morris et al.

It is certified that error appears in the above-identified patent and that said Letters Patent is hereby corrected as shown below:

Column 1,
Line 52, "gyms" should read --gyrus--

Column 3,
Line 15, "gyms" should read --gyrus--

Column 3,
Line 18, "gyms" should read --gyrus--

Column 3,
Line 24, "gyms" should read --gyrus--

Column 3,
Line 26, "gyms" should read --gyrus--

Column 3,
Line 28, "gyms" should read --gyrus--

Column 4,
Line 57, "gyms" should read --gyrus--

Column 7,
Line 30, "gyms" should read --gyrus--

Column 7,
Line 35, "gyms" should read --gyrus--

Column 7,
Line 65, "gyms:" should read --gyrus:--

Signed and Sealed this
Twenty-third Day of October, 2012

David J. Kappos
*Director of the United States Patent and Trademark Office*

Column 7,
Line 66, "gyms:" should read --gyrus:--

Column 9,
Line 64, "gyms" should read --gyrus--

Column 9,
Line 65, "gyms" should read --gyrus--

Column 9,
Line 67, "gyms and/or" should read --gyrus and/or--

Column 12,
Line 59, "gyms and left" should read --gyrus and left--

Column 12,
Line 59, "occipital gyms" should read --occipital gyrus--

Column 17,
Line 6, "gyms" should read --gyrus--

Column 19,
Line 47, "gyms" should read --gyrus--

Column 19,
Line 51, "Gyms" should read --Gyrus--

Column 2,
Line 54, "Gyms" should read --Gyrus--

Column 20,
Line 36, "occipital gyms" should read --occipital gyrus--

Column 20,
Lines 36-37, "temporal gyms" should read --temporal gyrus--

Column 20,
Line 42, "gyms" should read --gyrus--

Column 20,
Line 66, "gyms" should read --gyrus--

Column 21,
Line 23, "gyms" should read --gyrus--

CERTIFICATE OF CORRECTION (continued)
U.S. Pat. No. 8,239,000 B1

Column 21,
Line 24, "gyms" should read --gyrus--